United States Patent
Tsai et al.

(10) Patent No.: US 12,076,346 B2
(45) Date of Patent: Sep. 3, 2024

(54) HLA-F-MODIFIED CELLS AND METHODS

(71) Applicant: APPLIED STEMCELL, INC., Milpitas, CA (US)

(72) Inventors: Ruby Yanru Tsai, San Jose, CA (US); Alfonso Farruggio, Stanford, CA (US); Xiuling Chi, San Jose, CA (US); Kai Wang, Newark, CA (US)

(73) Assignee: APPLIED STEMCELL, INC., Milpitas, CA (US)

( * ) Notice: Subject to any disclaimer, the term of this patent is extended or adjusted under 35 U.S.C. 154(b) by 0 days.

(21) Appl. No.: 18/166,503

(22) Filed: Feb. 9, 2023

(65) Prior Publication Data

US 2023/0233610 A1 Jul. 27, 2023

Related U.S. Application Data

(63) Continuation of application No. 17/679,128, filed on Feb. 24, 2022, which is a continuation of application No. PCT/US2021/047219, filed on Aug. 23, 2021.

(60) Provisional application No. 63/069,141, filed on Aug. 23, 2020.

(51) Int. Cl.
| | |
|---|---|
| *A61K 35/17* | (2015.01) |
| *C07K 14/705* | (2006.01) |
| *C07K 14/74* | (2006.01) |
| *C07K 16/28* | (2006.01) |
| *C12N 5/0735* | (2010.01) |
| *G01N 33/50* | (2006.01) |

(52) U.S. Cl.
CPC ........ *A61K 35/17* (2013.01); *C07K 14/70539* (2013.01); *C07K 14/70575* (2013.01); *C07K 16/2896* (2013.01); *C12N 5/0606* (2013.01); *G01N 33/5014* (2013.01)

(58) Field of Classification Search
CPC ..................................................... A61K 35/17
See application file for complete search history.

(56) References Cited

U.S. PATENT DOCUMENTS

| | | |
|---|---|---|
| 2011/0274711 A1 | 11/2011 | Favier et al. |
| 2019/0125795 A1 | 5/2019 | Rosen et al. |
| 2019/0309259 A1 | 10/2019 | Meissner et al. |
| 2019/0345222 A1 | 11/2019 | Hirano et al. |
| 2019/0365876 A1 | 12/2019 | Russell et al. |

FOREIGN PATENT DOCUMENTS

| | | | |
|---|---|---|---|
| WO | 97/044667 A2 | 11/1997 | |
| WO | WO-2016044745 A1 * | 3/2016 | ......... A01K 67/0278 |
| WO | 2019/076149 A1 | 4/2019 | |
| WO | 2019/141862 A1 | 7/2019 | |

OTHER PUBLICATIONS

Dulberger et al. (2017, Immunity, vol. 46(6), pp. 1018-1029) (Year: 2017).*
Lin et al. (2019, Frontiers in Immunology, vol. 20, pp. 1-7) (Year: 2019).*
Tysoe-Calnon et al. (1991, Biochem J., vol. 277, pp. 359-369) (Year: 1991).*
Castella et al. (2019, Molecular Therapy—Methods & Clinical Dev., vol. 12, pp. 134-144) (Year: 2019).*
Somanchi et al. (2015, PLoS ONE, vol. 10(10), pp. 1-15). (Year: 2015).*
Tysoe-Calnon et al., "Molecular comparisons of the beta 2-microglobulin-binding site in class I major-histocompatibility-complex alpha-chains and proteins of related sequences", Biochem J. Jul. 15, 1991, vol. 277, No. 2, pp. 359-369, whole document.
International search report of PCT/US2021/047219.
Longmei Zhao et al, "Heterelogous expression of mutated HLA-G decreases immunogenicity of human embryonic stem cells and their epidermal derivatives", Stem Cell Research, Aug. 19, 2014, vol. 13, pp. 342-354.
Second Office Action for counterpart Chinese application No. 202180006714.1. mailed on Dec. 20, 2023.
Oral Clinical Immunology, 1st edition; Chen Wantao, Shanghai Jiao Tong University Press, pp. 57-58.
The third office action of the counterpart Chinese Application No. 202180006714.1, mailed on Apr. 18, 2024.

* cited by examiner

*Primary Examiner* — Anoop K Singh
*Assistant Examiner* — David A Montanari
(74) *Attorney, Agent, or Firm* — Jun He Law Offices P.C; James J. Zhu

(57) ABSTRACT

The present disclosure provides compositions and methods for cell transplantation therapy based on forced expression of an exogenous HLA-F protein in donor cells to be transplanted into a subject. In some embodiments, the donor cells express an exogenous chimeric HLA-F protein comprising an extracellular region comprising an HLA-F alpha 1 domain, an HLA alpha 2 domain, an HLA-F alpha 3 domain, a linker and a β2m protein.

8 Claims, 11 Drawing Sheets

Specification includes a Sequence Listing.

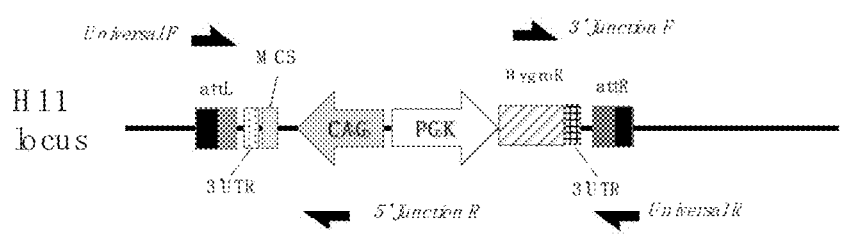
FIG. 8A
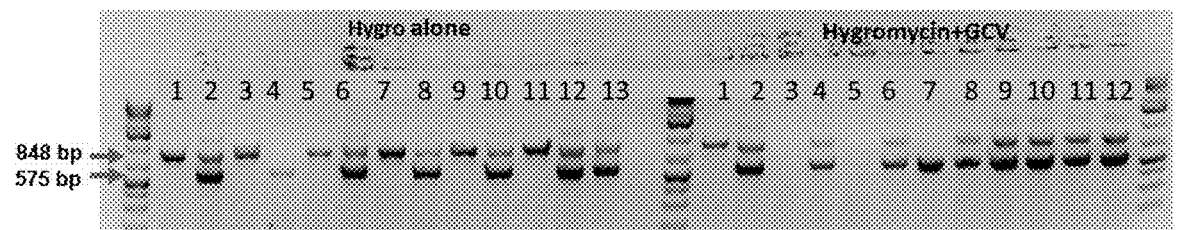
FIG. 8B
| | Hygromycin only | Hygromycin+GCV |
|---|---|---|
| Positive clone# | Clone#2, 6, 8, 10, 12, 13 | Clone#2, 4, 6, 8, 9, 10, 11, 12 |
| Locus specific integration% | 46% | 67% |
FIG. 8C

HLA-F-MODIFIED CELLS AND METHODS

CROSS-REFERENCE TO RELATED APPLICATIONS

This application is a continuation application of U.S. non-provisional patent application Ser. No. 17/679,128, which is a continuation application of PCT/US2021/047219, which claims priority to U.S. provisional patent application No. 63/069,141, filed Aug. 23, 2020, the disclosure of which are incorporated herein by reference.

SEQUENCE LISTING

The sequence listing that is contained in the file named "044903-8031US03-sequence listing-ST26", which is 58,146 bytes and was created on Dec. 1, 2022, is filed herewith by electronic submission and is incorporated by reference herein.

TECHNICAL FIELD

The present disclosure generally relates to cell biology, immunology and cell transplantation therapy. In particular, the present disclosure relates to compositions and methods for cell transplantation therapy based on forced expression of an exogenous HLA-F protein or a variant thereof in donor cells to be transplanted into a subject.

BACKGROUND OF THE INVENTION

Cell transplantation therapy is a procedure in which a patient receives donor cells in order to replace damaged cells or assert biological function by the donor cells. One of the major risks of cell transplantation therapy is the rejection of the transplanted cells by the recipient's immune system, especially when the donor cells are derived from a foreign host. To reduce the risk of transplantation rejection, it is generally required to match the type of classical human leukocyte antigen (HLA) class I and class II molecules between donor and recipient. However, it is often difficult to find a donor having a type of HLA molecules that well match the recipient. Although transplantation rejection to certain degree can be treated or ameliorated by immunosuppressants, the treatment of immunosuppressants often causes severe adverse effect.

Cell transplantation therapy has proven a big breakthrough for the treatment of intractable medical conditions such as blood cancer. Two T cell therapy engineered with chimeric antigen receptors (CARs)—Yescarta for non-Hodgkin lymphoma and B-cell acute lymphoblastic leukemia by Kite, a Gilead Company, and Kymriah for non-Hodgkin lymphoma by Novartis—were the first cell medicines approved by US FDA in 2017. However, these two approved cell therapies are autologous cell therapy: the therapeutic cells are taking from patient, modified ex vivo, and then transplanted back into the same patient to avoid immune rejection of donor cells. This personalized cell therapy is not only costly ($475,000 per treatment for Kymriah and $373,000 per treatment for Yescarta) but also time consuming, which in some cases the impact is life and death. If donor cells can be engineered to be hypoimmunogenic, these cells can be used for "off-the-shelf" allogeneic transplantation to more patients with reduced or no immune rejection. More importantly, patients will get timely life-saving treatment without the need to wait for cells to be engineered before transplantation. Therefore, a need exists for new compositions and methods for cell transplantation therapy.

SUMMARY OF THE INVENTION

The present disclosure in one aspect provides a genetically modified mammalian cell suitable for being transplanted to a subject in need thereof. In some embodiments, the genetically modified mammalian cell comprises an exogenous nucleic acid encoding an HLA-F protein or a variant thereof expressed on the cell surface of the genetically modified mammalian cell. In some embodiments, the genetically modified mammalian cell has reduced immunogenicity and/or improved immunosuppression as compared to a mammalian cell of the same-type without said exogenous nucleic acid. In some embodiments, the genetically modified mammalian cell can be used as a universal donor cell for treating various types of injuries or disorders, e.g., by reducing or eliminating the requirement for matching the type of classical HLA molecules between the donor cell and the recipient.

In some embodiments, the HLA-F protein is expressed as a chimeric HLA-F protein comprising an extracellular region comprising an HLA-F alpha 1 domain, an HLA alpha 2 domain, an HLA-F alpha 3 domain, and a β2m protein. In some embodiments, the HLA-F alpha 1 domain has a sequence of SEQ ID NO: 8, or a sequence having at least 90% identity thereto, or a sequence having 1, 2, 3 amino acid residue difference therefrom. In some embodiments, the HLA-F alpha 2 domain has a sequence of SEQ ID NO: 9, or a sequence having at least 90% identity thereto, or a sequence having 1, 2, 3 amino acid residue difference therefrom. In some embodiments, the HLA-F alpha 1 domain has a sequence of SEQ ID NO: 10 or 11, or a sequence having at least 90% identity thereto, or a sequence having 1, 2, 3 amino acid residue difference therefrom. In some embodiments, the β2m domain has a sequence of SEQ ID NO: 15, or a sequence having at least 90% identity thereto, or a sequence having 1, 2, 3 amino acid residue difference therefrom.

In some embodiments, the HLA-F alpha3 domain is linked to the β2m protein via a linker. In some embodiments, the linker has a sequence of SEQ ID NO: 16, or a sequence having at least 90% identity thereto, or a sequence having 1, 2, 3 amino acid residue difference therefrom. In some embodiments, the extracellular region of the chimeric HLA-F protein has an amino acid sequence of SEQ ID NO: 20 or 21 or a sequence having at least 90% identity thereto, or a sequence having 1, 2, 3 amino acid residue difference therefrom.

In some embodiments, the chimeric HLA-F protein further comprises a transmembrane domain. In some embodiments, the transmembrane domain has a sequence of SEQ ID NO: 12, or a sequence having at least 90% identity thereto, or a sequence having 1, 2, 3 amino acid residue difference therefrom.

In some embodiments, the chimeric HLA-F protein further comprises a cytoplasmic domain. In some embodiments, the transmembrane domain has a sequence of SEQ ID NO: 13 or 14, or a sequence having at least 90% identity thereto, or a sequence having 1, 2, 3 amino acid residue difference therefrom.

In some embodiments, the modified mammalian cell is a human cell, a mouse cell, a rat cell, a monkey cell or a pig cell. In some embodiments, the modified mammalian cell is a stem/progenitor cell. In some embodiments, the modified mammalian cell is an embryonic stem cell or induced pluripotent stem cell (iPS cell). In some embodiments, the modified mammalian cell is a fully differentiated cell. In some embodiments, the modified mammalian cell is a fully differentiated cell differentiated from a stem/progenitor cell, e.g., an iPS cell. In some embodiments, the modified mammalian cell is a T cell or NK cell.

In some embodiments, the genetically modified mammalian cell further comprises an exogenous nucleic acid encoding an HLA-G protein. In some embodiments, the HLA-G protein is a chimeric HLA-G protein comprising an extracellular region which comprises an HLA-G alpha 1 domain, an HLA-G alpha 2 domain, an HLA-G alpha 3 domain and a beta-2 microglobulin (β2m) protein. In some embodiments, the HLA-G alpha 1 domain has a sequence of SEQ ID NO: 24, or a sequence having at least 90% identity thereto, or a sequence having 1, 2, 3 amino acid residue difference therefrom. In some embodiments, the HLA-F alpha 2 domain has a sequence of SEQ ID NO: 25, or a sequence having at least 90% identity thereto, or a sequence having 1, 2, 3 amino acid residue difference therefrom. In some embodiments, the HLA-F alpha 1 domain has a sequence of SEQ ID NO: 26, or a sequence having at least 90% identity thereto, or a sequence having 1, 2, 3 amino acid residue difference therefrom.

In some embodiments, the HLA-G alpha3 domain is linked to the β2m protein via a linker. In some embodiments, the linker has a sequence of SEQ ID NO: 16, or a sequence having at least 90% identity thereto, or a sequence having 1, 2, 3 amino acid residue difference therefrom.

In some embodiments, the chimeric HLA-G protein further comprises a transmembrane domain. In some embodiments, the transmembrane domain has a sequence of SEQ ID NO: 27, or a sequence having at least 90% identity thereto, or a sequence having 1, 2, 3 amino acid residue difference therefrom.

In some embodiments, the chimeric HLA-G protein further comprises a cytoplasmic domain. In some embodiments, the transmembrane domain has a sequence of SEQ ID NO: 28, or a sequence having at least 90% identity thereto, or a sequence having 1, 2, 3 amino acid residue difference therefrom.

In some embodiments, the chimeric HLA-G protein has an amino acid sequence of SEQ ID NO: 29, or a sequence having at least 90% identity thereto, or a sequence having 1, 2, 3 amino acid residue difference therefrom.

In some embodiments, the genetically modified mammalian cell further comprises an exogenous nucleic acid encoding CD95L. In some embodiments, the CD95L has a sequence of SEQ ID NO: 31, or a sequence having at least 90% identity thereto, or a sequence having 1, 2, 3 amino acid residue difference therefrom.

In some embodiments, the modified mammalian cell further comprises a chimeric antigen receptor (CAR). In some embodiments, the modified mammalian cell is a CAR-T cell or a CAR-NK cell. In some embodiments, the CAR-T cell or the CAR-NK cell is differentiated from an iPS cell.

In some embodiments, the HLA-F protein or a variant thereof is expressed by the genetically modified mammalian cell for at least 5, 6, 7, 8, 10, 15, 20, 25, or 50 weeks.

In some embodiments, the reduced immunogenicity and/or improved immunosuppression of the genetically modified mammalian cell as compared to the mammalian cell without said exogenous nucleic acid is determined by a NK cell cytotoxicity assay.

In another aspect, the present disclosure provides a method of cell transplantation therapy. In some embodiments, the method comprises injecting, implanting, or grafting to a subject in need thereof a cellular or tissue composition comprising a population of genetically modified cells, wherein the genetically modified cells comprise an exogenous nucleic acid encoding an HLA-F protein described herein which is expressed on the surface of the genetically modified cells. In some embodiments, the HLA-F protein is express as a chimeric HLA-F protein comprising an HLA-F alpha 1 domain, an HLA alpha 2 domain, an HLA-F alpha 3 domain, and a β2m protein. In some embodiments, the subject has at least one mismatched classical HLA class I or HLA class II molecule as compared to the genetically modified cells. In some embodiments, the population of genetically modified cells exhibit reduced immunogenicity and/or improved immunosuppression as compared to cells of the same-type without said exogenous nucleic acid.

In some embodiments, at least one mismatched classical HLA class I or HLA calls II molecule is selected from the group consisting of HLA-A, HLA-B, HLA-C, HLA-DP, HLA-DQ and HLA-DR.

In some embodiments, the reduced immunogenicity and/or improved immunosuppression is determined by a NK cell cytotoxicity assay.

In some embodiments, the population of genetically modified cells are differentiated from stem/progenitor cells (e.g., embryonic stem cells or iPS cells) in vitro. In some embodiments, the population of genetically modified cells are T cells or NK cells. In some embodiments, the population of genetically modified cells are CAR-T cells or CAR-NK cells.

In some embodiments, the population of genetically modified cells are not rejected by the subject's immune system for at least 2, 4, 6, 8, 10, 12, 14, 16, 18, 20, 24, 36, 48 or 52 weeks.

BRIEF DESCRIPTION OF DRAWINGS

The accompanying drawings, which are incorporated herein, form part of the specification. Together with this written description, the drawings further serve to explain the principles of, and to enable a person skilled in the relevant art(s), to make and use the present disclosure.

FIG. 5A shows the heterodimer of HLA-F non-covalently bound with β2m. FIG. 5B shows the HLA-F fused to β2m by a 15 amino acid linker. FIG. 5C shows the design of the HLA-F-β2m fusion protein comprising an HLA-F alpha 1 domain, an HLA-F alpha 2 domain, an HLA-F alpha 3 domain, linked to a β2m protein by a 15 amino acid linker followed by a transmembrane domain and a cytoplasmic domain.

Figure 6:
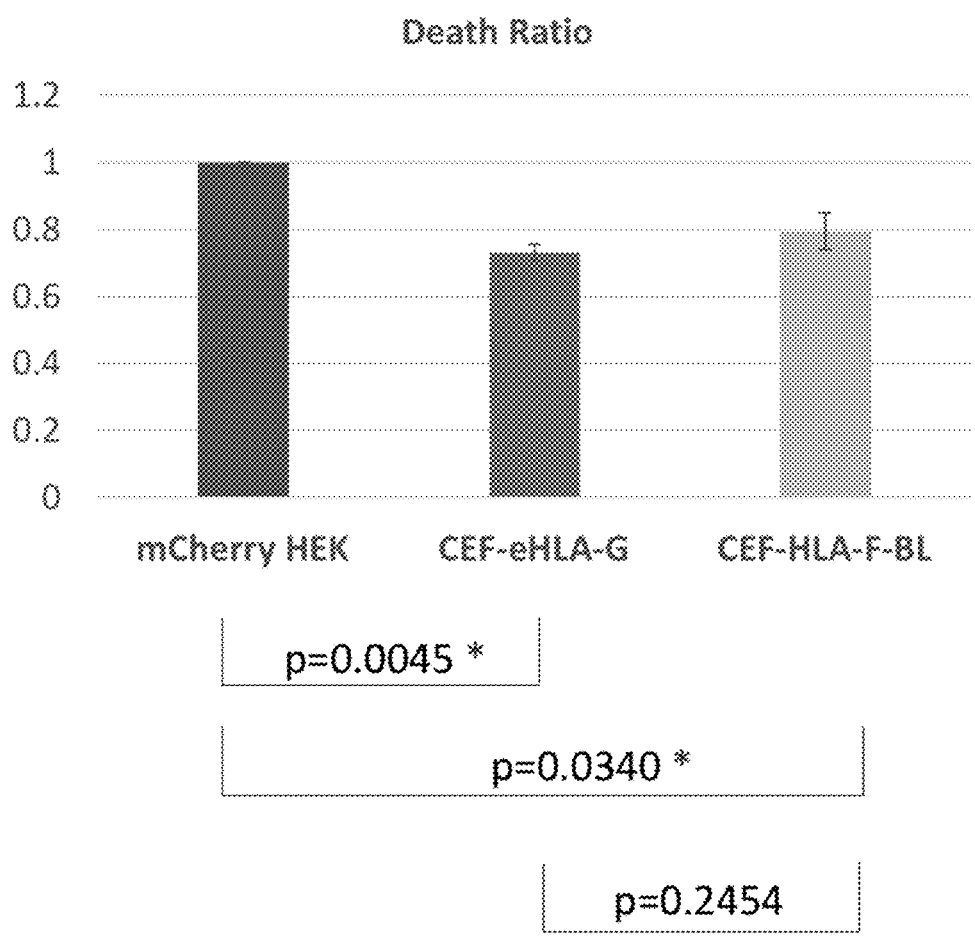

FIG. 6 illustrates that the expression of exogenous chimeric HLA-F protein in HKE293 cells reduced NK cell mediated cytotoxicity.

Figure 7:
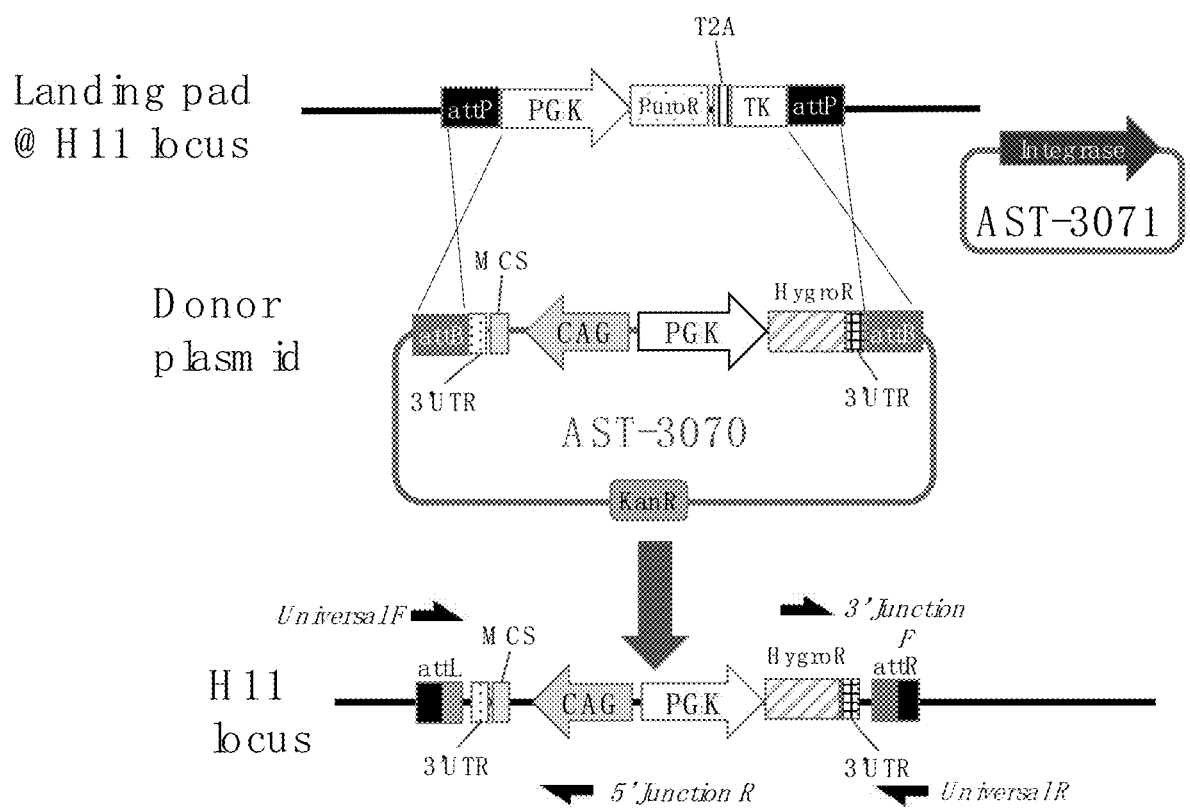

FIG. 7 illustrates a schematic of generating site-specific gene insertion in TARGTT master iPSC line. Transgene is cloned at the MCS (multiple cloning site) in AST-3070 donor plasmid, and co-transfected with AST-3071 integrase plasmid. Upon recombination between attP and attB, the transgene is inserted at the H11 locus.

FIGS. 8A, 8B and 8C illustrate the confirmation of site-specific CAG-MCS integration. FIG. 8A shows the genomic region including genotyping primers after site-specific gene insertion. FIG. 8B shows the PCR gel electrophoresis using 2 sets of primers at the 5' and 3' junction indicating site-specific gene insertion band, 575 bp and 848 bp. FIG. 8C shows the genotyping results.

Figure 9:
Figure 9:
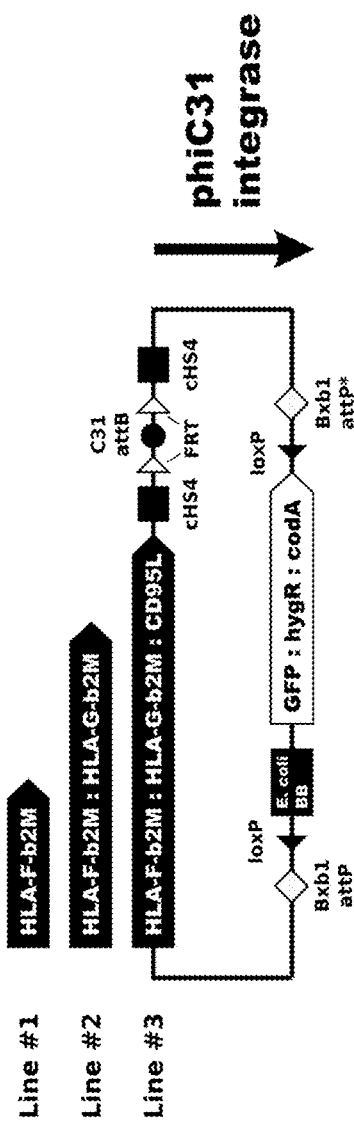
Figure 9:
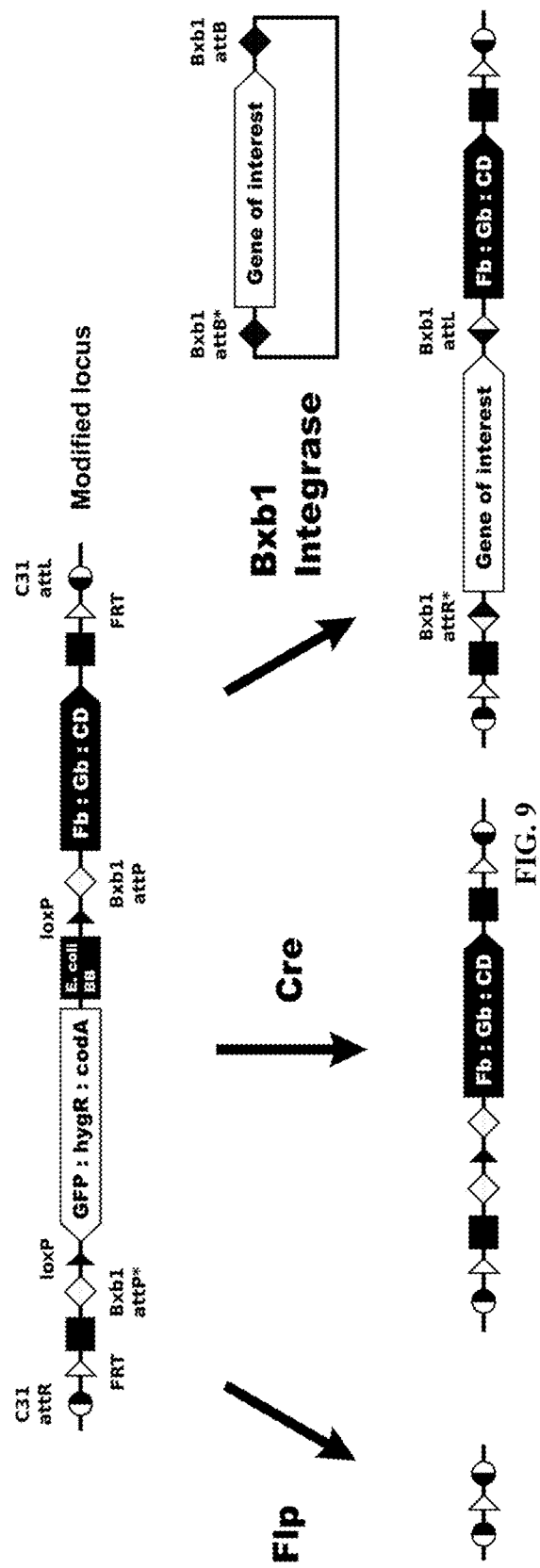

FIG. 9 illustrates the schematic design of modified iPSC lines. Line 1 contains HLA-F-β2m and HLA-G-β2m; and Line 2 contains HLA-F-β2m, HLA-G-β2m and CD95L.

Figure 10:
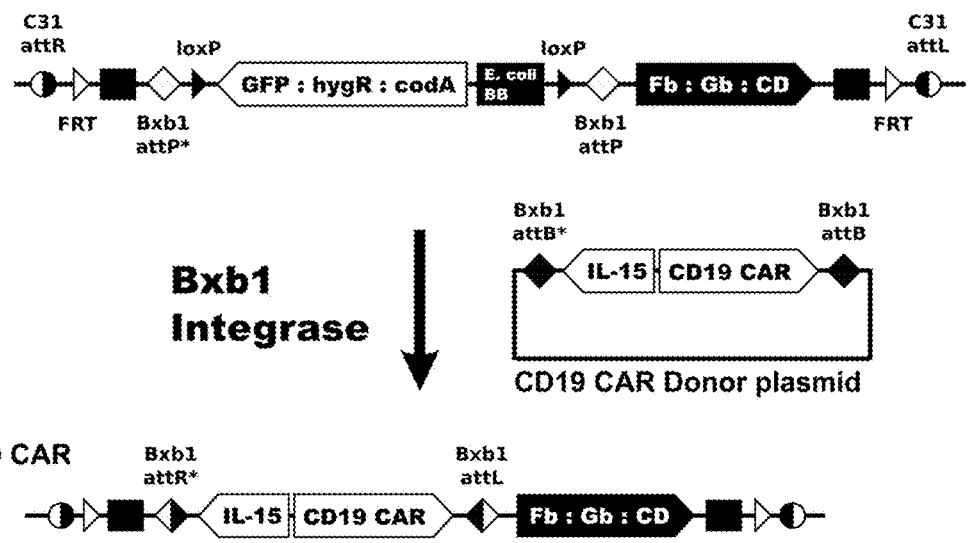

FIG. 10 illustrates the schematic design of CD19CAR-iNK. With Bxb1 integrase, the attB sites on the donor plasmid expressing CD19CAR and IL-15 recombine with the Bxb1 attP sites in the iPSC genome. This results in replacement of the GFP reporter cassette with the CD19CAR-IL15 cassette. *in attP* and attB* represents different core sequences form attP and attB to control directional recombination.

Figure 11:
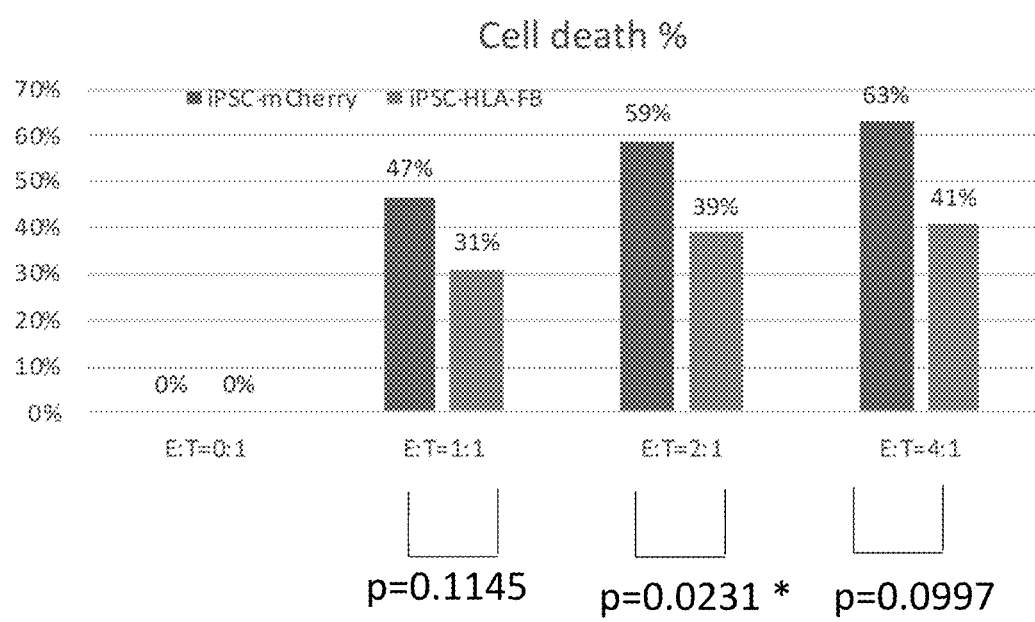

FIG. 11 illustrates that overexpression of HLA-F has immune-repression activity in iPSCs. Similar NK-mediated toxicity assays were performed using iPSC that express HLA-F-β2M (HLA-FB) except that CD56+NK cells were used as effector cells instead of PBMC. Several ratios, including 1:1, 2:1 and 4:1 of effector (NK cells) versus target cells (iPSC) were used. Each group contain 3 samples. The ratio of effector:target=2:1 showed lower cell death of 39% from 59% with a "p" value of 0.0231, indicating statistically significant immune protection from HLA-FB expression.

DETAILED DESCRIPTION OF THE INVENTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Definition

The following definitions are provided to assist the reader. Unless otherwise defined, all terms of art, notations and other scientific or medical terms or terminology used herein are intended to have the meanings commonly understood by those of skill in the art. In some cases, terms with commonly understood meanings are defined herein for clarity and/or for ready reference, and the inclusion of such definitions herein should not necessarily be construed to represent a substantial difference over the definition of the term as generally understood in the art.

As used herein, the singular forms "a", "an" and "the" include plural references unless the context clearly dictates otherwise.

"Antigen" refers to a molecule that provokes an immune response. This immune response may be either humoral, or cell-mediated response, or both. The skilled artisan will understand that any macromolecule, including virtually all proteins or peptides, can serve as an antigen. It is readily apparent that the present disclosure includes autoantigens acting as antigen eliciting immune response.

"Allogeneic" cells refer to any cells derived from a different subject of the same species.

The term "chimeric antigen receptor" or "CAR" as used herein refers to an artificially constructed hybrid protein or polypeptide containing an antigen binding domain of an antibody (e.g., a single chain variable fragment (scFv)) linked to a domain or signaling, e.g., T-cell signaling or T-cell activation domains, that activates an immune cell, e.g., a T cell or a NK cell (see, e.g., Kershaw et al., supra, Eshhar et al., Proc. Natl. Acad. Sci. USA, 90(2): 720-724 (1993), and Sadelain et al., Curr. Opin. Immunol. 21(2): 215-223 (2009)). CARs are capable of redirecting the immune cell specificity and reactivity toward a selected target in a non-MHC-restricted manner, taking advantage of the antigen-binding properties of monoclonal antibodies. The non-WIC-restricted antigen recognition confers immune cells expressing CARs on the ability to recognize an antigen independent of antigen processing, thus bypassing a major mechanism of tumor escape. In addition, when expressed in T-cells, CARs advantageously do not dimerize with endogenous T-cell receptor (TCR) alpha and beta chains.

"HLA" or "Human Leucocyte Antigen" refers to a group of related proteins that are encoded by the major histocompatibility complex (MHC) gene complex in humans, which are responsible for the regulation of the immune system. HLA genes can be classified into class I and class II genes. HLA class I genes include three major genes, i.e., HLA-A, HLA-B and HLA-C, and three minor genes, i.e., HLA-E, HLA-F and HLA-G genes. β2m protein binds with major and minor class I HLA protein to produce a heterodimer. HLA class II genes include three major genes, i.e., HLA-DP, HLA-DQ and HLA-DR genes, and two minor genes, i.e., HLA-DM and HLA-DO genes. The class II HLA proteins combine to form heterodimeric (αβ) protein receptors that are typically expressed on the surface of antigen-presenting cells.

Percentage of "identity" or "sequence identity" in the context of polypeptide or polynucleotide is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

"Operatively linked" refers to a functional relationship between two or more polynucleotide sequences. In the context of a polynucleotide encoding a protein, such as a polypeptide chain of an HLA-F protein of the disclosure, the term means that the two or more polynucleotide sequences are joined such that the amino acid sequences encoded by these segments remain in-frame. In the context of transcriptional or translational regulation, the term refers to the functional relationship of a regulatory sequence to a coding sequence, for example, a promoter in the correct location and orientation to the coding sequence so as to modulate the transcription.

"Immunogenicity" or "immunogenic" refers to the ability of a foreign substance, such as an antigen, to provoke an immune response in the body of a subject. The immunogenic response typically includes both cell-mediated and antibody-mediated immune response.

"Polynucleotide" or "nucleic acid" refers to a chain of nucleotides. As used herein polynucleotides include all polynucleotide sequences which are obtained by any means available in the art, including, without limitation, recombinant means and synthetic means.

"Polypeptide," and "protein" are used interchangeably, and refer to a chain of amino acid residues covalently linked by peptide bonds. The polypeptides include natural peptides, recombinant peptides, synthetic peptides, or a combination thereof.

"T cell receptor" or "TCR" refers to a protein complex on the surface of T cells that is responsible for recognizing fragments of antigen as peptides bound to MHC molecules.

"Therapeutically effective amount" or "effective amount" refers to an amount of cells, composition, formulation or any material as described here effective to achieve a desirable biological result. Such results may include, without limitation, replacing damaged cell, allowing improvement in the overall condition of the subject, and stimulating tissue regeneration or repair.

A "variant" of a protein, e.g., HLA-F, as used herein refers to a protein having an amino acid sequence different from its parent protein from which the variant is derived, but keeps the biological function as the parent protein. Examples of a variant include, without limitation, a fusion protein comprising the parent protein, and a mutant of the parent protein. In some embodiments, the variant has a sequence of at least 70%, 80%, 90%, 95%, 96%, 97%, 98%, 99% identity to the parent protein, or a sequence having 1, 2, 3, 4, 5, 6, 7, 8, 9, or 10 amino acid residue difference from the parent protein.

"Vector" refers to a vehicle into which a polynucleotide may be operably inserted so as to deliver, replicate or express the polynucleotide. A vector may contain a variety of regulatory elements including, without limitation, origin of replication, promoter, transcription initiation sequences, enhancer, selectable marker genes, and reporter genes. A vector may also include materials to aid in its entry into a host cell, including but not limited to a viral particle, a liposome, or ionic or amphiphilic compounds.

It is noted that in this disclosure, terms such as "comprises", "comprised", "comprising", "contains", "containing" and the like have the meaning attributed in United States Patent law; they are inclusive or open-ended and do not exclude additional, un-recited elements or method steps. Terms such as "consisting essentially of" and "consists essentially of" have the meaning attributed in United States Patent law; they allow for the inclusion of additional ingredients or steps that do not materially affect the basic and novel characteristics of the claimed invention. The terms "consists of" and "consisting of" have the meaning ascribed to them in United States Patent law; namely that these terms are close ended.

Genetically Modified Cells

Cell transplantation therapy is a promising therapeutic approach for the treatment of a variety of intractable disease or disorders such as cancer, diabetes, heart disease and neurodegenerative diseases. One of the major obstacles that prevent cell transplantation therapy from implementing in clinic is immune rejection of donor cells. The major immunological hurdle to the transplantation of allogeneic cells and tissues is the expression of the highly polymorphic human leukocyte antigen (HLA) genes, including HLA class I and II. The functions of HLA class I antigens are involved in presenting antigens to T cells and serving as ligands for a panel of immune receptors expressed on natural killer (NK) cells, T cells, and myeloid cells (Boudreau J E & Hsu K C 2018; Pecht I 2018.). HLA class I molecules play a central role in allogeneic rejection through their presentation of peptide antigens to CD8+ T cells. The heterodimeric structure of HLA class I molecules with a common β2 microglobulin (β2M) subunit paired with different heavy chain molecules. The HLA class I family can be further grouped as the classical HLA-Ia, including HLA-A, -B, and -C molecules and non-classical antigens HLA-Ib, including HLA-E, -F, and -G molecules. In contrast to the highly polymorphic HLA-Ia antigens that are expressed on all nucleated cells, HLA-Ib molecules are characterized by particular tissue localizations, low genetic diversity, a limited peptide repertoire, and functional profile (Persson et al. 2017). Cells that downregulate HLA class I molecules can be detected and eliminated by NK cells, which is initiated when inhibitory receptors, such as CD94/NKG2A, on NK cells fail to bind to HLA class I molecules (Bix et al. 1991; Liao et al. 1991).

To avoid or minimize transplantation rejection, it is generally required to match the type of classical HLA class I and class II molecules between donor and recipient. However, finding a donor having a type of HLA molecules that well match the recipient is often difficult.

The present disclosure is in part based on the discovery that the need for autologous or carefully patient-matched cell lines could be circumvented by engineering a single HLA-engineered iPSC (induced pluripotent stem cell) or ESC (embryonic stem cell) line that can escape allogeneic responses and lysis by NK cells. Induced pluripotent stem cells (iPSCs) have the potential to be differentiated to all cell types of the human body. In some embodiments, the universal donor cells are hypoimmunogenic iPSCs generated by engineering a single HLA molecule. In some embodiments, the iPSCs are modifiable by engineering a landing pad for future gene insertion. These universal modifiable iPS cells (UM-iPSC) can then be differentiated to a specific cell type and provide off-the-shelf cell medicine.

Therefore, the present disclosure in one aspect provides a genetically modified mammalian cell suitable to be used as a universal donor cell by reducing or eliminating the requirement for matching the type of classical HLA molecules between the donor cell and the recipient. In some embodiments, the genetically modified mammalian cell expresses specific nonpolymorphic HLA class I molecules, such as the class 1b molecules HLA-E, HLA-F, HLA-G and a variant thereof, which can inhibit NK cell-mediated lysis without stimulating an allogeneic response. HLA-E binds to and presents peptides from the signal sequences of other HLA class I proteins and is a ligand for the CD94/NKG2A receptor (Lee et al. 1998; Braud et al. 1998). Gornalusse et al. (2017) has shown that forced expression of minimally polymorphic HLA-E molecules in human PSCs (pluripotent stem cells), which were previously eliminated of surface expression of all class I molecules, confers hypo-immunogenicity to these cells and their differentiated variants. These HLA-E engineered cells are not recognized as allogeneic by CD8+ T cells, do not bind anti-HLA antibodies and are resistant to NK-mediated lysis. Their study provides a potential source of universal cells for cell transplantation therapies. HLA-G is normally expressed on the surface of placental cytotrophoblasts that do not express HLA-A, B or C, and it protects these cells from NK cell-mediated lysis by interacting with the inhibitory receptors KIR2DL4 and ILT2 (Narvarro et al. 1999; Pazmany et al. 1996; Raj agopalan & Long 1999). U.S. Pat. No. 9,714,280 has shown that overexpression of HLA-G in human ESCs persistently provides the cells with characteristics of reduced immunogenicity and/or improved immunosuppression, such that these cells have the promise of being universal or improved donor cells for transplants, cellular and tissue regeneration or reconstruction.

Less is known about the function of HLA-F. Since the discovery of HLA-F in 1990 by Geraghty and coworkers (Geraghty et al. 1990), only a small amount of evidence for its clinical relevance has been obtained (Kochan et al. 2013). For example, the genetic variants and protein expression of HLA-F have been observed to be associated with different types of diseases, such as cancer (Wu et al. 2017; Tang et al, 2012; Zhang et al. 2013), infection (Laaribi et al. 2018; Lunemann et al. 2018), reproduction, and autoimmune disorders (Shobu et al. 2006; Hackmon et al. 2017; Santos et a. 2018; Afroz et al, 2017). Elevated HLA-F expression has been found in cancer lesions and peripheral blood, which was associated with poor survival in cancer patients (Zhang et al. 2013; Wu et al. 2018). HLA-F has been implicated as a protective molecule in pregnancy (Burrows et al. 2016) and the peripheral nervous system, where HLA-F recognition by the inhibitory KIR3DL2 was shown to prevent motor neuron death in the development of amyotrophic lateral sclerosis (ALS) (Song et al. 2016).

In some embodiments, the genetically modified mammalian cell comprises an exogenous nucleic acid encoding an HLA-F protein. In some embodiments, the HLA-F protein is expressed as a chimeric protein comprising an HLA-F alpha 1 domain, an HLA alpha 2 domain, an HLA-F alpha 3 domain, and a $\beta 2m$ protein. In some embodiments, the genetically modified mammalian cell has reduced immunogenicity and/or improved immunosuppression as compared to a mammalian cell of the same-type without said exogenous nucleic acid.

HLA-F and the Chimeric HLA-F Protein

HLA-F belongs to nonclassical class I HLA heavy chain molecules. Class I HLA (or MHC-I) molecules function by binding and displaying self and non-self peptides on the cell surface where they designate the cell as healthy, infected, or foreign. Leukocytes, such as T cells and NK cells, perceive the information presented by HLA class I molecules via a diverse array of antigen receptors to elicit the appropriate immune response. While classical class I HLA molecules (HLA-A, HLA-B, and HLA-C) are ubiquitously expressed, the nonclassical class I HLA molecules (HLA-E, HLA-F and HL-G) are much more specialized in terms of tissue localization, antigen presentation, and function. Because of their limited levels of polymorphism, the repertoire of peptides that nonclassical class I HLA molecules present is greatly reduced and they predominantly regulate immunity though TCR (T cell receptor)-independent interactions. HLA-F has been observed only in a subset of cell membranes, mostly B cells and activated lymphocytes. As a result, it has been suggested that its role involves association with specialized ligands that become available in the cell membrane of activated cells. For example, HLA-F can act as a peptide binding of ILT2 and ILT4.

Figure 3:
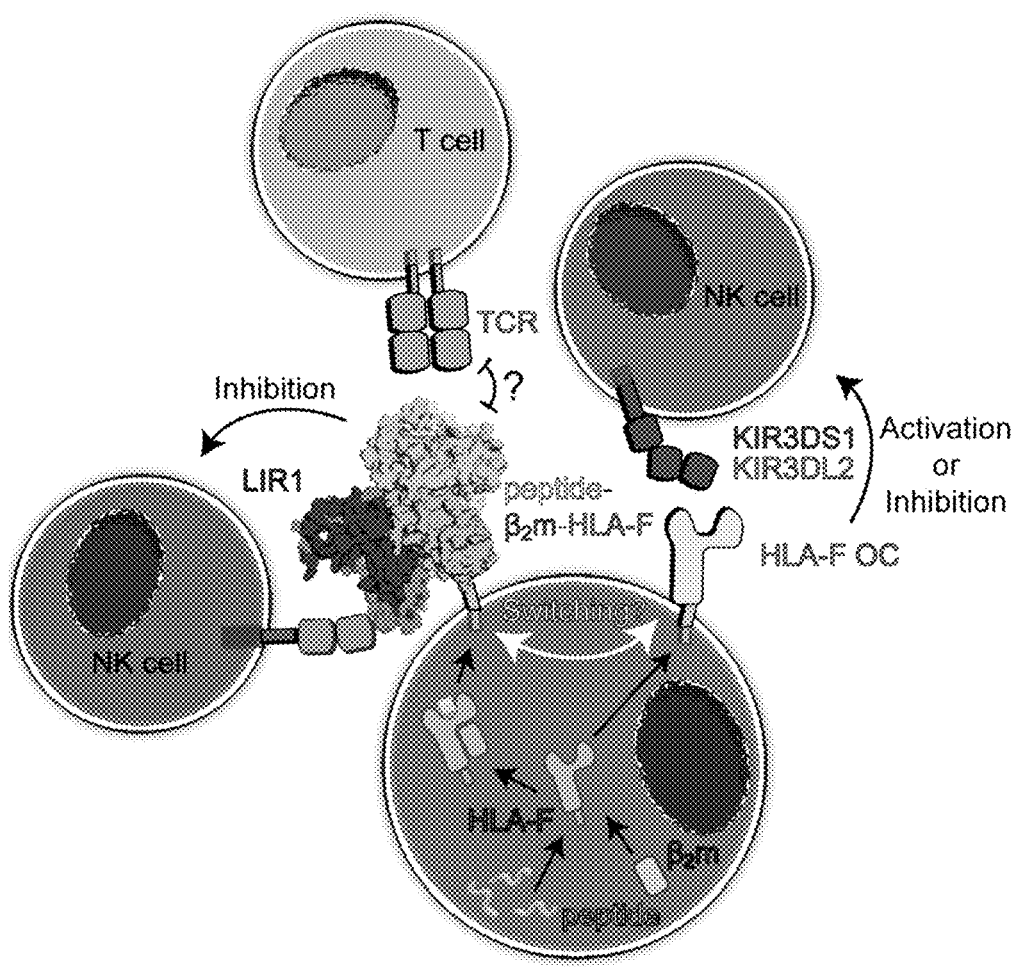
FIG. 3 is a schematic that illustrates a mode of peptide presentation of HLA-F molecule. Peptide-bound HLA-F and empty HLA-F open conformer (OC) molecules are recognized by distinct receptors on NK cells.
Figure 4:
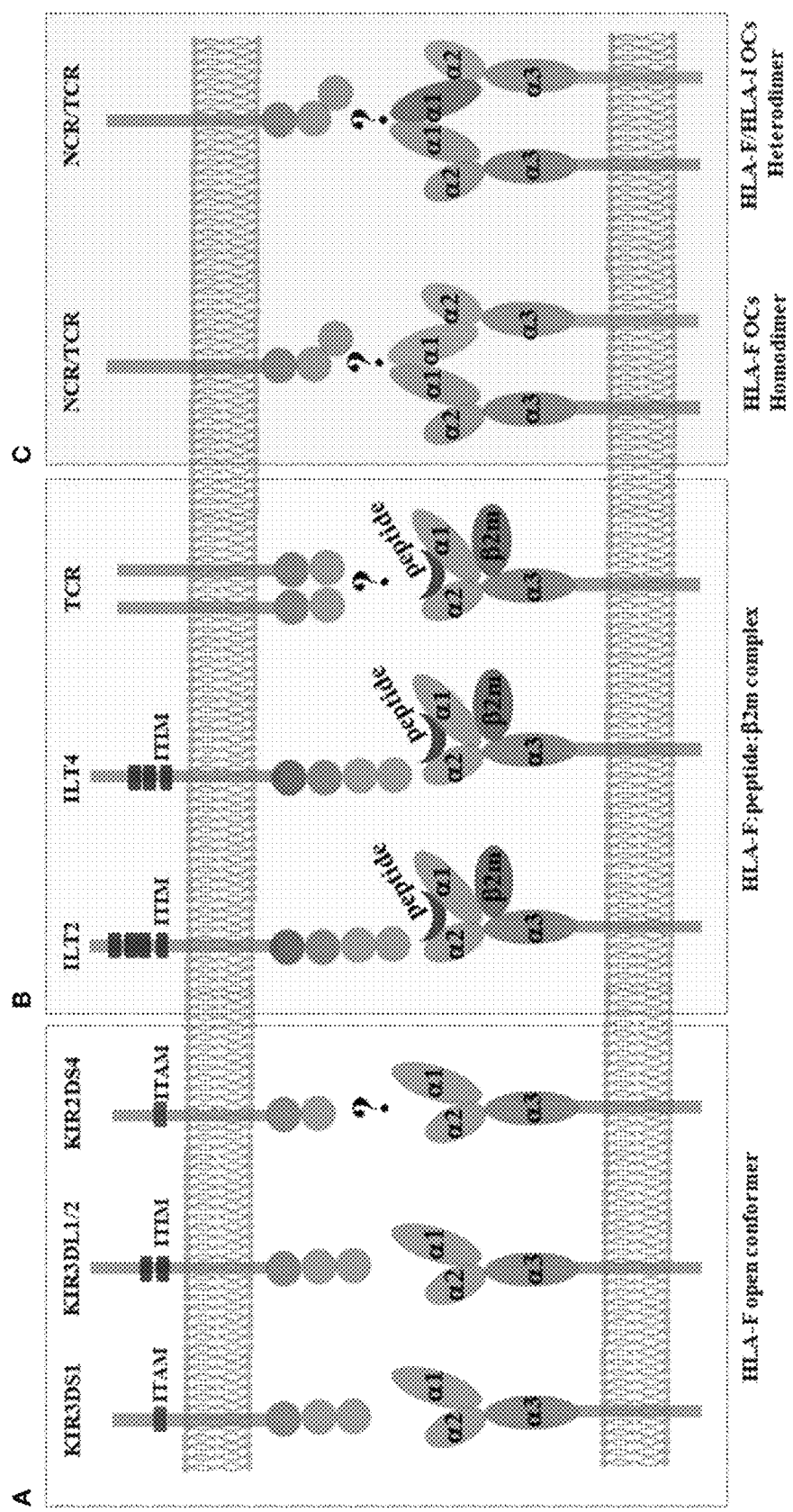
FIG. 4 is a schematic that illustrates the interaction of HLA-F molecules with a diverse panel of receptors on immune cells such as NK cells. HLA-F molecules can have different conformation form and form different complexes, which can interact with both activating and inhibitory receptors on the immune cells.

Akin to other HLA family members, HLA-F molecules apparently can interact with both activating and inhibitory receptors on immune cells such as NK cells and can present a diverse panel of peptides to T cells (Goodridge et al. 2013; Leptin et al. 2000; Dulberger et al. 2017). Crystal structure of HLA-F reveals a unique mode of peptide presentation (Dulberger etal 2017). In this scenario, the open conformers (OCs) of HLA-F molecules have been observed to directly bind to immune inhibitory receptors (KIR3DL1/2 and ILT2) and immune-activating receptors (KIR2DS4 and KIR3DS1) on NK cells (Leptin et al. 2000; Burian et al. 2016). Additionally, HLA-F has been shown to present peptides to T cells and to regulate immunity through interactions with distinct NK cell receptors, depending on the molecular conformation of peptide-bound HLA-F or HLA-F OCs (FIG. 3). In fact, NK receptors (NKRs) differentiate between peptide bound and peptide-free (or OC) HLA-F. The complex structure of peptide loaded 2M-HLA-F, but not OCs, bound to the inhibitory LIR1 (FIG. 3). These important findings provide new evidence that HLA-F functions as an important immune regulatory molecule in human physiological and pathological conditions (Sim and Sun 2017; Vely et al. 2016).

Figure 1:
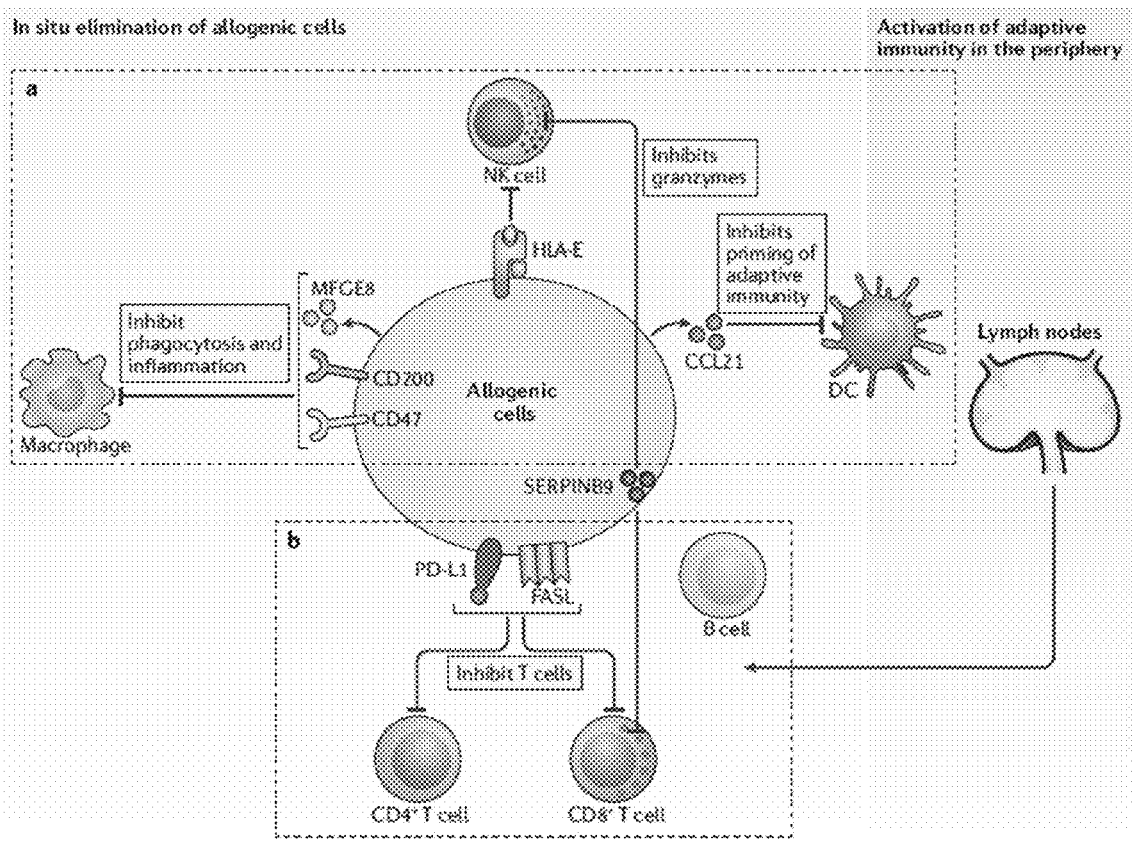
FIG. 1 is a schematic that illustrates the innate and adaptive immune modulation pathways involved in immune recognition and reactions to allografts.
Figure 2:
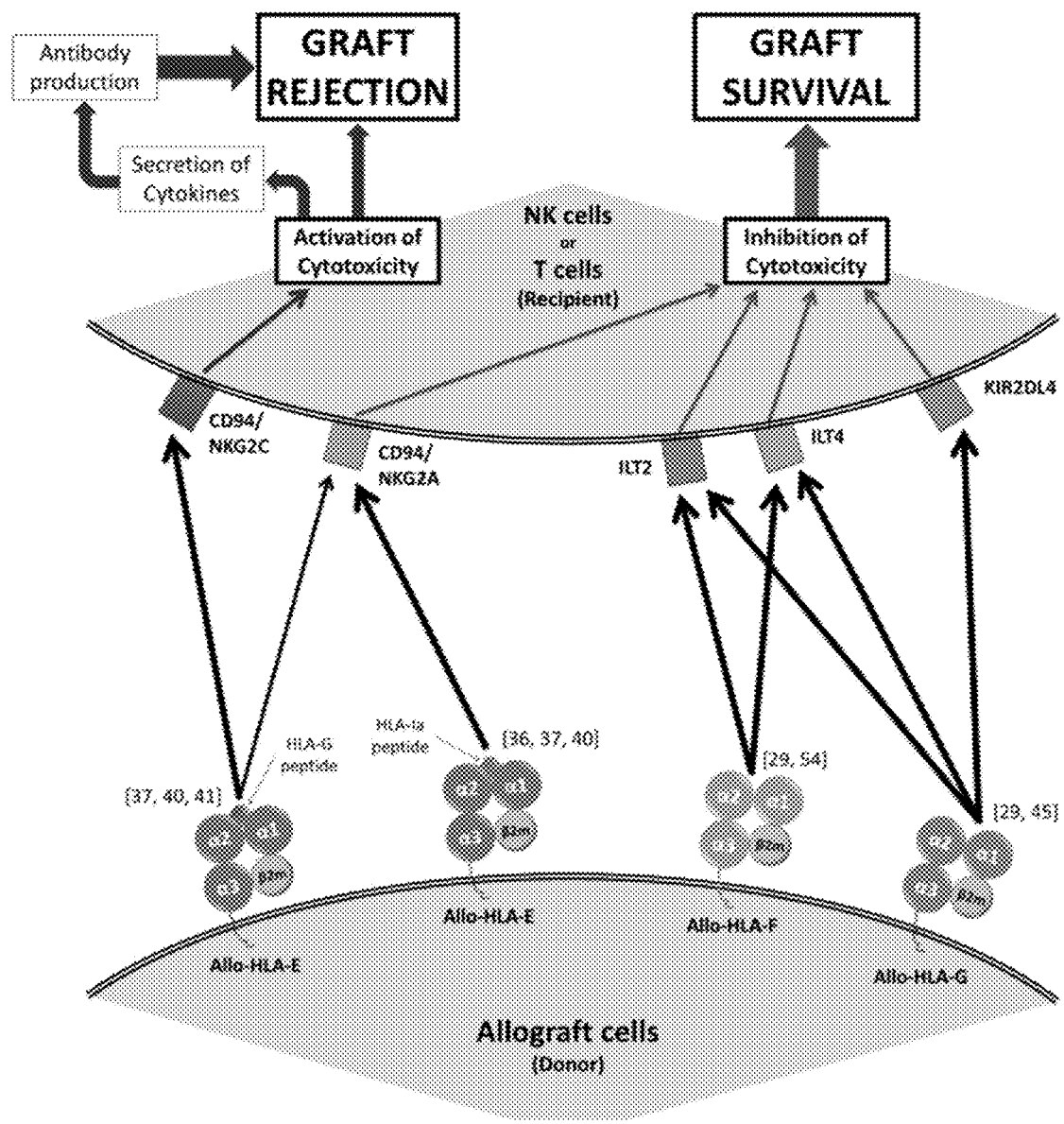
FIG. 2 is a schematic that illustrates the interaction of the HLA molecules on the allograft cells and their respective potential receptors/partners on the immune cells (e.g., NK cells and T cells) of the recipient.

Immune modulation is a complex process, and many factors are involved in immune recognition and reactions to allografts besides HLA molecules. The rejection of allogeneic cells involves both innate immune cells, such as macrophages and NK cells as well as adaptive immune cells such as CD4+ and CD8+ T cells and B cells (FIG. 1) (Lanza et al. 2019). Innate immune cells can attack allogeneic cells rapidly, whereas adaptive immune cells are primed and expanded in the peripheral lymph organs before migrating to the site of engraftment. Both innate and adaptive immune cells reject allogenic cells in situ using a variety of cytotoxic mechanisms. Immune cloaking strategies found in nature use specific immunomodulatory factors to inhibit these pathways and escape rejection. Non-polymorphic HLA class I molecules like HLA-E, F, and G can suppress NK cell activity and immune checkpoint molecules such as programmed cell death 1 ligand 1 (PD-L1) and the apoptosis-inducing tumor necrosis factor family member FASL (CD95) can suppress or kill CD4+ and CD8+ lymphocytes. Intracellular molecules like SERPINB9, a serine protease inhibitor (the human orthologue of the Spi6 mouse gene) can inhibit granzyme B, and chemokines such as CCL21 can disrupt the migration of dendritic cells (DCs) and suppress their ability to prime adaptive immunity. Molecules like milk-fat globule EGF-factor 8 (MFGE8) and the surface molecules CD47 (also known as integrin-associated protein) and membrane glycoprotein CD200 can inhibit the phagocytosis of cells by monocytes and macrophages and impair the ability of monocytes and macrophages to produce proinflammatory molecules. Combination of inhibiting several immunogenicity pathways is likely to improve allogeneic engraftment.

HLA-F has been implicated as a protective molecule in pregnancy (Burrows et al., PLoS Genetics, 2016) and the peripheral nervous system, where HLA-F recognition by the inhibitory KIR3DL2 was shown to prevent motor neuron death in the development of amyotrophic lateral sclerosis (ALS) (Song et al., Nat Med, 2016). It has also been shown that recognition of HLA-F by the activating KIR3DS1 on NK cells elicits an anti-viral response that inhibits HIV-r replication (Garcia-Beltran et al., Nat Immunol. 2016).

In the class I HLA family there are ten conserved residues that are critical for establishing the architecture for specific interactions with peptide residues being presented. Five of these ten residues are altered within the HLA-F groove. It has been suggested that HLA-F may exist in multiple isoforms with varying potential for peptide binding and recognition by antigen receptors. The crystal structure of HLA-F reveals that HLA-F can exist as both an open conformer (OC) and as a bona fide peptide-presenting MHC molecule. Peptide-bound HLA-F and empty HLA-F OC are recognized by distinct NK cell receptors (Dulberger et al., Immunity, 2018).

As used herein, the HLA-F protein exogenously expressed in the genetically modified cell can be either a naturally occurring HLA-F protein or an engineered HLA-F protein modified from the naturally occurring HLA-F protein.

A naturally occurring HLA-F comprises from N-terminus to C-terminus: an HLA-F alpha 1 domain, an HLA alpha 2 domain, an HLA-F alpha 3 domain, a transmembrane domain and a cytoplasmic domain. The HLA-F alpha 1 domain and HLA alpha 2 domain form the groove of peptide binding. The HLA-F alpha 3 domain associates with beta-2 microgloblin, which is necessary for the stability of HLA-F complex. In some embodiments, the naturally occurring HLA-F protein has an amino acid sequence of SEQ ID NO: 1, 2, 3 or 4. In some embodiments, the HLA-F protein is encoded by a polynucleotide sequence of SEQ ID NO: 5.

In some embodiments, the HLA-F protein is a chimeric protein. As used herein a chimeric HLA-F protein refers to a protein modified from HLA-F in which a second polypeptide (i) is fused or inserted to the HLA-F protein or (ii) replaces a region of amino acids of HLA-F protein. In some embodiments, the chimeric HLA-F protein comprises an extracellular region comprising an HLA-F alpha 1 domain, an HLA alpha 2 domain, an HLA-F alpha 3 domain, and a β2m protein. In some embodiments, the HLA-F alpha 1 domain has an amino acid sequence of SEQ ID NO: 8 or a sequence having at least 80%, 85%, 90%, 95%, or 99% identity thereto, or a sequence having 1, 2, 3, 4 or 5 amino acid residues difference therefrom. In some embodiments, the HLA alpha 2 domain has an amino acid sequence of SEQ ID NO: 9 or a sequence having at least 80%, 85%, 90%, 95%, or 99% identity thereto, or a sequence having 1, 2, 3, 4 or 5 amino acid residues difference therefrom. In some embodiments, the HLA-F alpha 3 domain has an amino acid sequence of SEQ ID NO: 10 or 11, or a sequence having at least 80%, 85%, 90%, 95%, or 99% identity thereto, or a sequence having 1, 2, 3, 4 or 5 amino acid residues difference therefrom. In some embodiments, the β2m protein has an amino acid sequence of SEQ ID NO: 15 or a sequence having at least 80%, 85%, 90%, 95%, or 99% identity thereto, or a sequence having 1, 2, 3, 4 or 5 amino acid residues difference therefrom.

In some embodiments, the HLA-F alpha 3 domain linked to the β2m protein via a linker. In some embodiments, the linker comprises a glycine-serine (GS) doublet between 2 and 20 amino acid residues in length. Exemplary the linker comprises $(G_4S)_3$.

In some embodiments, the extracellular region of the chimeric HLA-F protein has an amino acid sequence of SEQ ID NO: 20 or 21, or a sequence having at least 80%, 85%, 90%, 95%, or 99% identity thereto.

In some embodiments, the chimeric HLA-F protein further comprises a transmembrane domain. In some embodiments, the transmembrane domain of the chimeric HLA-F protein is the transmembrane domain of a naturally occurring HLA-F protein. In some embodiments, the transmembrane domain has a sequence of SEQ ID NO: 12, or a sequence having at least 80%, 85%, 90%, 95%, or 99% identity thereto. It can be understood that the transmembrane domain of the chimeric HLA-F protein described herein may be derived from any membrane-bound or transmembrane protein including, but are not limited to, BAFFR, BLAME (SLAMF8), CD2, CD3 epsilon, CD4, CD5, CD8, CD9, CD11a (CD18, ITGAL, LFA-1), CD11b, CD11c, CD11d, CD16, CD19, CD22, CD27, CD28, CD29, CD33, CD37, CD40, CD45, CD49a, CD49d, CD49f, CD64, CD80, CD84, CD86, CD96 (Tactile), CD100 (SEMA4D), CD103, CD134, CD137 (4-1BB), CD150 (IPO-3, SLAMF1, SLAM), CD154, CD160 (BY55), CD162 (SELPLG), CD226 (DNAM1), CD229 (Ly9), CD244 (2B4, SLAMF4), CD278 (ICOS), CEACAM1, CRT AM, GITR, HYEM (LIGHTR), IA4, IL2R beta, IL2R gamma, IL7R a, ITGA1, ITGA4, ITGA6, ITGAD, ITGAE, ITGAM, ITGAX, ITGB1, ITGB2, ITGB7, KIR, LTBR, OX40, NKG2C, NKG2D, NKp30, NKp44, NKp46, NKp80 (KLRF1), PAG/Cbp, PSGL1, SLAMF6 (NTB-A, Ly108), SLAMF7, an alpha, beta or zeta chain of a T-cell receptor, TNFR2, VLA1, and VLA-6. In certain embodiments, the transmembrane domain of the chimeric HLA-F protein described herein is synthetic, e.g., comprising predominantly hydrophobic residues such as leucine and valine.

In some embodiments, the chimeric HLA-F protein further comprises a cytoplasmic domain. In some embodiments, the cytoplasmic domain of the chimeric HLA-F protein described herein is the cytoplasmic domain of a naturally occurring HLA-F protein. In some embodiments, the cytoplasmic domain has a sequence of SEQ ID NO: 13 or 14, or a sequence having at least 80%, 85%, 90%, 95%, or 99% identity thereto.

In some embodiments, the chimeric HLA-F protein comprises from the N-terminus to the C-terminus: a HLA-F alpha 1 domain, a HLA alpha 2 domain, a HLA-F alpha 3 domain, linker, a β2m protein, a transmembrane domain and an intracellular domain. In certain embodiments, the chimeric HLA-F protein has an amino acid sequence of SEQ ID NO: 17 or 18, or a sequence having at least 80%, 85%, 90%, 95%, or 99% identity thereto. In some embodiments, the chimeric HLA-F protein is encoded by a polynucleotide sequence of SEQ ID NO: 19, or a sequence having at least 70%, 75%, 80%, 85%, 90%, 95%, or 99% identity thereto.

Genetic Modified Cells Expressing HLA-F

As disclosed herein, a wide range of mammalian cells that express the HLA-F proteins described herein can be generated. The cell types that can be used for such modification include, without limitation, totipotent cells, embryonic stem cells (e.g., human embryonic stem cells) and differentiated cells, induced pluripotent stem cells (iPS cells) and differentiated cells, multipotent stem cells, epidermal progenitor cells, mesenchymal stem cells, pancreatic β cell progenitors, pancreatic β cells, cardiac progenitors, cardiomyocytes, hepatic progenitors, hepatocytes, muscle cell progenitors, muscle cells, kidney cells, osteoblasts, hematopoietic progenitors, dental follicle cells, hair follicle cells, retinal pigment epithelial cells, neural stem cells, neurons, astrocytes, oligodendrocytes, microglia, inner ear cells, and fibroblasts (e.g., dermal fibroblast). In some embodiments, the genetically modified cells are cells having an immune system cell type such as lymphocytes, natural killer cells, macrophage, and dendritic cells. Such mammalian cells can be derived from one of several species including, e.g., human, mouse, rat, monkey, or pig. In essence, any cell types can be modified to express exogenous HLA-F protein or the variant thereof, which has reduced immunogenicity and/or improved immunosuppression as compared to a mammalian cell of the same-type without expressing the exogenous HLA-F protein or the variant thereof.

In some embodiments, to obtain a substantially enriched population of genetically modified cells of a desired cell type expressing exogenous HLA-F or variant thereof, a genetically modified pluripotent stem cell line such as a human embryonic stem cell line, or a human induced pluripotent stem cell line, or any cell line that has multipotent traits including mesenchymal stem cells and immune system progenitor cells, that expresses HLA-F or the variant thereof is generated and then subjected to directed differentiation to obtain a cell population that expresses HLA-F or the variant thereof and that is substantially enriched for a desired cell type. In some embodiments, the substantially enriched cell population includes at least about 2% to about 100% of the desired cell type, e.g., at least about 3%, 4%, 5%, 7%, 8%, 10%, 20%, 22%, 25%, 35%, 40%, 45%, 50%, 60%, 70%, 75%, 80%, 85%, or another percentage of the desired cell type from at least about 2% to about 100%. Methods for enriching cells of a desired cell type are known in the art. See, e.g., U.S. Pat. No. 8,647,871 to Hantash.

Methods for obtaining human embryonic stem cells or induced pluripotent stem cells are known in the art, as described in, e.g., U.S. Pat. Nos. 6,200,806 and 7,217,569 (for human embryonic stem cell derivation) and U.S. Pat. Nos. 8,048,999, 8,058,065, and 8,048,675 (for generation of human induced pluripotent stem cells).

The genetically modified mammalian cells, e.g., pluripotent or multipotent stem cell lines and also fully differentiated mammalian cells, that stably express an HLA-F protein encoded by an exogenous nucleic acid can be generated by any of a number of methods known in the art.

In some embodiments, the genetically modified cells can be generated by stable transfection with one or more nucleic acid expression vectors comprising the nucleic acid encoding the HLA-F protein or the variant thereof described herein. The nucleic acid encoding the HLA-F protein or the variant thereof can be inserted into different types of vectors known in the art, for example, a plasmid, a phagemid, a phage variant, a viral vector derived from animal virus, a cosmid, transposon, a site directed insertion vector (e.g., CRISPR, Zinc finger nucleases, TALEN), or a suicide expression vector. In some embodiments, the vector is a DNA or RNA.

In some embodiment, the nucleic acid encoding the HLA-F protein or the variant thereof is operatively linked to at least one regulatory polynucleotide element in the vector for expression of the HLA-F or the variant thereof. Typical vectors contain various regulatory polynucleotide elements, for example, elements (e.g., transcription and translation terminators, initiation sequences, and promoters) regulating the expression of the inserted nucleic acid, elements (e.g., origin of replication) regulating the replication of the vector in a host cell, and elements (e.g., terminal repeat sequence of a transposon) regulating the integration of the vector into a host genome.

The expression of the HLA-F can be achieved by operably linking the nucleic acid encoding the HLA-F to a promoter, and incorporating the construct into a vector. Suitable promoters include, but are not limited to, the Chinese hamster elongation factor-1 alpha (CHEF-1a) promoter (see Running Deer et al (2004), Biotechnol. Prog., 20:880-889; and GenBank Accession No. AY 188393.1), the M-U3/R-variant promoter of the Murine Stem Cell Virus (MSCV) promoter (as described in Swindle et al (2004), J Biol Chem, 279:34-41), the phosphoglycerate kinase (PGK) promoter, the human (3-actin promoter, the ubiquitin C promoter, a CMV promoter, and a SV40 promoter, and a MMTV promoter.

In some embodiments, the promoter used to drive expression of an exogenous HLA-F transgene is expressed in one or more desired cell types at a level that is higher than in other cell types. One of ordinary skill in the art will appreciate that, for example, where an HLA-F modified stem cell is to be differentiated into a particular cell type, it may be advantageous to select a promoter that is active within or even selective for that particular cell type. For example, for a given tissue or cell type-selective promoter the expression level may be about two fold to 100 fold higher in the desired cell type compared to another cell type, e.g., about 3 fold, 4 fold, 5 fold, 10 fold, 20 fold, 25 fold, 30 fold, 40 fold, 50 fold, 70 fold, 80 fold, 90 fold, or another fold higher level of expression in the desired cell type compared to another cell type. Examples of tissue and/or cell type-selective promoters include, but are not limited to, the promoters for: Neuron-Specific Enolase (neuronal), Synapsin (neuronal), CamKII (forebrain neurons), HB9 (motor neurons), and Dopamine Transporter (dopaminergic neurons); Glial Fibrillary Acidic Protein (astrocytes); Albumin (liver); a-Myosin Heavy Chain (a-MHC-cardiomyocytes); Neurogenin 3 and Pancreas-Duodenum Homeobox 1 (pancreas); Keratin 14 (skin); and Bestrophinl (retinal pigment epithelium).

In order to assess the expression of the HLA-F protein, the vector can also comprise a selectable marker gene or a reporter gene or both for identification and selection of the cells to which the vector is introduced. Examples of suitable selectable markers encoded by such vectors include proteins that confer resistance to a selection agent. Such proteins and their corresponding selection agents include, without limitation, puromycin N-acetyltransferase (puromycin), hygromycin phosphotransferase (hygromycin), blasticidin-S-deaminase (blasticidin), and neomycin phosphotransferase (neomycin). Useful reporters include, for example, luciferase, beta-galactosidase, chloramphenicol acetyl transferase, secreted alkaline phosphatase, or the green fluorescent protein gene.

In some embodiments, the vector is a viral vector. Viral vectors may be derived from, for example, retroviruses, adenoviruses, adeno-associated viruses (AAV), herpes viruses, and lentiviruses. Useful viral vectors generally contain an origin of replication functional in at least one organism, a promoter, restriction endonuclease sites, and one or more selectable markers. In some embodiments, the vector is a retrovirus vector, such as lentiviral vector. Lentiviral vector is particular useful for long-term, stable integration of the polynucleotide encoding the HLA-F into the genome of non-proliferating cells that result in stable expression of the HLA-F protein in the genetically modified cell.

In some embodiments, the vector is a transposon-based expression vector. A transposon is a DNA sequence that can change its position within a genome. In a transposon system, the nucleic acid encoding the HLA-F is flanked by terminal repeat sequences recognizable by a transposase which mediates the movement of the transposon. A transposase can be co-delivered as a protein, encoded on the same vector as the HLA-F, or encoded on a separate vector. Non-limiting examples of transposon systems include Sleeping Beauty, Piggyback, Frog Prince, and Prince Charming.

In some embodiments, the vector is a recombinase or integrase-based expression vector. A recombinase or integrase is a highly specialized enzyme that promotes DNA rearrangement between specific target sites (Greindley et al., 2006; Esposito, D., and Scocca, J. J. *Nucleic Acids Research* (1997) 25, 3605-3614; Nunes-Duby, S. E., et al. *Nucleic Acids Research* (1998) 26, 391-406; Stark, W. M., et al. *Trends in Genetics* (1992) 8, 432-439). In a recombinase or integrase system, the nucleic acid encoding the HLA-F or the variant thereof is operably linked to a first recombinase recognition site which facilitates the recombination between the first recombinase recognition site and a second recombinase recognition site at a target locus to which the nucleic acid encoding the HLA-F or the variant thereof is inserted. A recombinase or integrase can be co-delivered as a protein or mRNA, encoded on the same vector as the HLA-F, or encoded on a separate vector. Non-limiting examples of recombinase/integrase systems include Cre, Flp, phiC31, Bxb1, and Tn3.

A vector can be introduced into a mammalian cell by any method known in the art, for example, by physical, chemical or biological means. Physical methods for introducing a polynucleotide into a host cell include calcium phosphate precipitation, lipofection, particle bombardment, microinjection, electroporation, and the like. Biological methods include the use of viral vectors, and especially retroviral vectors, for inserting genes into mammalian, e.g., human cells. Chemical means include colloidal dispersion systems, such as macromolecule complexes, nanocapsules, microspheres, beads, and lipid-based systems including oil-in-water emulsions, micelles, mixed micelles, lip nanoparticles, and liposomes.

The genetically modified mammalian cells expressing exogenous HLA-F protein, as described herein, have reduced immunogenicity relative to corresponding mammalian cells that do not express the exogenous HLA-F. For example, immunogenicity may be reduced by at least about 5% to about 95%, relative to a corresponding cell type that does not express exogenous HLA-F, e.g., about 6%, 7%, 10%, 12%, 15%, 20%, 30%, 40%, 50%, 65%, 70%, 80%, 85%, 90%, or another percent reduced immunogenicity relative to cells of the same cell type that do not express exogenous HLA-F.

Methods for determining immunogenicity of cells are known in the art. For example, in some embodiments, HLA-F modified mammalian cells (e.g., human induced pluripotent stem cells, or differentiated cells from HLA-F modified induced pluripotent stem cells, or cells that are already fully differentiated prior to modification, etc.) or unmodified mammalian cells are cultured in the presence of an allogenic natural killer cell line (e.g., NK-92) and then cytotoxicity to the HLA-F modified versus unmodified cells by the NK-92 cells is determined by any of a number of standard cell viability assays.

Compositions Comprising Genetically Modified Cells

Also provided in the present disclosure are pharmaceutical compositions, topical compositions, cellular grafts, and artificial tissues comprising or generated using one or more HLA-F modified mammalian cells.

The stable and persistent HLA-F expression provided the genetically modified cells with reduced immunogenicity and/or improved immunosuppression. In addition, the modified mammalian cells can be differentiated from genetically modified stem/progenitor cells and also have stable and persistent HLA-F expression that provides reduced immunogenicity and/or improved immunosuppression. Thus, the HLA-F modified cells described herein can be used to generate universal donor cells of any type, whether from directed differentiation of a genetically modified pluripotent or multipotent cell, or from genetic modification of a fully differentiated cell.

In some embodiment, a therapeutic composition for cancer treatment is provided that comprises a genetically modified CAR-T or CAR-NK cells expressing an exogenous HLA-F protein as described herein. The expression of the CAR (e.g., a CAR directed to CD19) in the genetically modified CAR-T or CAR-NK cells directed the CAR-T or CAR-NK cells specificity and reactivity toward a selected target in a non-MHC-restricted manner, while the expression of HLA-F or the variant thereof avoids or decreases the risk of transplantation rejection, making the composition a universal donor for allogeneic cancer immunotherapy. In some embodiments, the genetically modified CAR-T or CAR-NK cells are differentiated from stem/progenitor cells, such as iPS cells in vitro. In some embodiments, the stem/progenitor cells, such as iPS cells are genetically modified to express the CAR and the exogenous HLA-F protein or the variant thereof.

In some embodiments, a topical composition for skin regeneration or repair is provided that comprises a genetically modified dermal fibroblast cell expressing an exogenous HLA-F protein or the variant thereof as described herein. In another aspect, a pharmaceutical composition for injection is provided that comprises a genetically modified dermal fibroblast cell expressing an exogenous HLA-F protein or the variant thereof as described herein. In another aspect, a skin graft composition is provided that comprises a genetically modified dermal fibroblast cell expressing an exogenous HLA-F protein or the variant thereof as described herein. In another aspect, a permanent skin graft composition is provided that comprises a genetically modified embryonic epidermal progenitor cell expressing an exogenous HLA-F protein or the variant thereof as described herein.

Method of Treatment

In one aspect, the present disclosure provides a method for cell transplantation therapy. As the genetically modified cells expressing the exogenous HLA-F or the variant thereof described herein have reduced immunogenicity and/or increased immunosuppression, these traits allow the modified cell to serve as a universal or improved donor cell or tissue. This is because the HLA-F mediated reduction of immunogenicity and/or improvement in immunosuppression provided to the cell can reduce or eliminate the requirement of matching the type of classical human leukocyte antigen (HLA) class I and class II molecules between donor cells and the recipient for numerous injuries, diseases, or disorders. Thus, HLA-F modified cells that stably express HLA-F protein (e.g., a chimeric HLA-F protein described herein) may be used as a universal donor cell for therapy.

The therapy may be directed at treating the cause of the disease; or alternatively, the therapy may be to treat the effects of the disease or condition. The genetically modified cells may be transferred to, or close to, an injured site in a subject; or the cells can be introduced to the subject in a manner allowing the cells to migrate, or home, to the injured site. The transferred cells may advantageously replace the damaged or injured cells and allow improvement in the overall condition of the subject. In some instances, the transferred cells may stimulate tissue regeneration or repair, including skin regeneration or skin repair. In some instances, the transferred cells carry therapeutic molecules targeting and eliminating disease causing cells, for example, cancer cells.

In some embodiments, the HLA-F modified mammalian cells described herein are administered to a subject suffering from any of a number of conditions including, but not limited to cancer, cardiovascular disease, eye disease (e.g., macular degeneration), auditory disease, (e.g., deafness), diabetes, neurodegenerative disease, Alzheimer's Disease, Parkinson's Disease, multiple sclerosis, osteoporosis, liver disease, kidney disease, autoimmune disease, arthritis, gum disease, a dental condition, or a proliferative disorder (e.g., a cancer). In other cases, the subject is suffering from, or at high risk of suffering from, an acute health condition, e.g., stroke, spinal cord injury, burn, or a wound. In other cases, the subject is suffering from loss of tissue such as lipoatrophy or aging-related losses in collagen. In other cases, the subject suffers from a non-healing ulcer, or is need for an agent to assist in closure of defects like hypospadias. In other cases, the subject is need for a permanent or temporary skin graft for wound healing or for skin substitutes.

In one aspect, the present disclosure provides a universal method of cellular or tissue grafting to a subject in need thereof, the method comprising injecting or grafting to the subject a cellular or tissue composition comprising a population of HLA-F modified cells, wherein the subject has at least one mismatched classical HLA class I or HLA class II molecule as compared to the population of HLA-F modified cells, and wherein the population of HLA-F modified cells exhibits reduced immunogenicity and/or improved immunosuppression as compared to cells of the same-type without the HLA-F modification. The reduced immunogenicity and/or improved immunosuppression can be determined, for example, by comparing the HLA-F modified cell to a control cell of the same type without the HLA-F modification in an NK-92 cytotoxicity assay, a humanized NSG tumor growth assay, and/or a PBMC proliferation assay.

In another aspect, the present disclosure provides a method for regenerating skin to a subject in need thereof, the method comprising injecting a population of HLA-F modified dermal fibroblasts and/or HLA-F modified embryonic epidermal progenitors to a site of skin injury on the subject, wherein the subject has at least one mismatched classical HLA class I or HLA class II molecule as compared to the population of HLA-F modified dermal fibroblasts and or HLA-F modified embryonic epidermal progenitors, In another aspect, the present disclosure provides a method for treating cancer in a subject in need thereof, the method comprising administering a population of HLA-F modified CAR-T or CAR-NK cell to the subject. The CAR (e.g., a CAR directed to CD19) is capable of re-directing the specificity and reactivity of the T cells or NK cells toward a selected cancer cell. The expression of HLA-F makes the modified CAR-T or CAR-NK universal donors in an allogeneic cancer immunotherapy, i.e., the subject may have at least one mismatched classical HLA class I or HLA class II molecule as compared to the HLA-F modified CAR-T or CAR-NK cells. In some embodiments, the genetically modified CAR-T or CAR-NK cells are differentiated in vitro from iPS cells which are genetically modified to express the CAR and the exogenous HLA-F protein.

HLA-F modified cell types to be administered to a subject in need thereof include, but are not limited to, lymphocytes, natural killer cells, macrophage, dendritic cells, epidermal progenitor cells, mesenchymal stem cells, pancreatic β cell progenitors, pancreatic β cells, cardiac progenitors, cardiomyocytes, hepatic progenitors, hepatocytes, muscle cell progenitors, muscle cells, kidney cells, osteoblasts, hematopoietic progenitors, dental follicle cells, hair follicle cells, retinal pigment epithelial cells, neural stem cells, neurons, astrocytes, oligodendrocytes, microglia or any combination thereof. Such mammalian cells can be derived from one of several species including, e.g., human, mouse, rat, monkey, or pig.

The therapy may be directed at treating the cause of the disease; or alternatively, the therapy may be to treat the effects of the disease or condition. The HLA-F modified cells may be transferred to, or close to, an injured site in a subject; or the cells can be introduced to the subject in a manner allowing the cells to migrate, or home, to the injured site. The transferred cells may advantageously replace the damaged or injured cells and allow improvement in the overall condition of the subject. In some instances, the transferred cells may stimulate tissue regeneration or repair. In some instances, the transferred cells carry therapeutic molecules targeting and eliminating disease causing cells, for example, cancer cells.

The transferred cells may be cells differentiated from HLA-F modified pluripotent (or totipotent) stem cells. The transferred cells also may be multipotent stem cells differentiated from pluripotent, HLA-F modified cells.

The number of administrations of treatment to a subject may vary. Introducing the HLA-F modified and/or differentiated cells into the subject may be a one-time event; but in certain situations, such treatment may elicit improvement for a limited period of time and require an on-going series of repeated treatments. In other situations, multiple administrations of the cells may be required before an effect is observed. As will be appreciated by those of ordinary skill in the art, the exact treatment protocols will depend upon the disease or condition, and the stage of the disease and parameters of the individual subject being treated.

The HLA-F modified cells may be introduced to the subject via any of the following routes: parenteral, intravenous, intraarterial, intramuscular, subcutaneous, transdermal, intratracheal, intraperitoneal, or into spinal fluid.

The HLA-F modified cells may be differentiated into cells and then transferred to subjects suffering from a wide range of diseases or disorders.

CAR-T or CAR-NK cells have been used to treat cancer (see, e.g., Kershaw et al., supra, Eshhar et al., supra, and Sadelain et al., supra). In some embodiments, HLA-F modified CAR-T or CAR-NK cells derived from HLA-F modified iPS cells expressing a CAR are administered to a subject suffering from cancer.

Pancreatic islet cells (or primary cells of the islets of Langerhans) may be transplanted into a subject suffering from diabetes (e.g., diabetes mellitus, type 1), see e.g., Burns et al, (2006) Curt Stem Cell Res. Ther., 2:255-266. Thus, in some embodiments, pancreatic beta cells derived from HLA-F modified cells are transplanted into a subject suffering from diabetes (e.g., diabetes mellitus, type 1).

In other examples, hepatic cells or hepatic stem cells derived from HLA-F modified cells are transplanted into a subject suffering from a liver disease, e.g., hepatitis, cirrhosis, or liver failure.

Degenerative heart diseases such as ischemic cardiomyopathy, conduction disease, and congenital defects could benefit from stem cell therapies. See, e.g., Janssens et al, (2006), Lancet, 367: 1 13-121.

Hematopoietic cells or hematopoietic stem cells (HSCs) derived from HLA-F modified cells may be transplanted into a subject suffering from cancer of the blood, or other blood or immune disorder. Examples of cancers of the blood that are potentially treated by hematopoietic cells or HSCs include: acute lymphoblastic leukemia, acute myeloblastic leukemia, chronic myelogenous leukemia (CML), Hodgkin's disease, multiple myeloma, and non-Hodgkin's lymphoma. Often, a subject suffering from such disease must undergo radiation and/or chemotherapeutic treatment in order to kill rapidly dividing blood cells. Introducing HSCs derived from HLA-F modified cells to these subjects may help to repopulate depleted reservoirs of cells.

Subjects suffering from neurological diseases or disorders could especially benefit from HLA-F modified cell therapy, especially when the blood brain barrier may have been compromised. In some approaches, the HLA-F modified cells may be differentiated into neural stem cells or neurons or microglia and then transplanted to an injured site to treat a neurological condition, e.g., Alzheimer's disease, Parkinson's disease, multiple sclerosis, cerebral infarction, spinal cord injury, or other central nervous system disorder, see, e.g., Morizane et al, (2008), Cell Tissue Res., 33 1(1):323-326; Coutts and Keirstead (2008), Exp. Neurol., 209(2):368-377; Goswami and Rao (2007), Drugs, 10(10):713-719.

For the treatment of Parkinson's disease, the HLA-F modified cells may be differentiated into dopamine-acting neurons and then transplanted into the striate body of a subject with Parkinson's disease. For the treatment of multiple sclerosis (MS), neural stem cells may be differentiated into oligodendrocytes or progenitors of oligodendrocytes, which are then transferred to a subject suffering from MS.

For the treatment of any neurologic disease or disorder, a successful approach may be to introduce neural stem cells to the subject. For example, in order to treat Alzheimer's disease, cerebral infarction or a spinal injury, the HLA-F modified cells may be differentiated into neural stem cells followed by transplantation into the injured site. The HLA-F modified cells may also be engineered to respond to cues that can target their migration into lesions for brain and spinal cord repair, e.g., Chen et ah, (2007), Stem Cell Rev, 3(4):280-288.

Optionally, the HLA-F modified cells used in the cell transplantation therapies also express a reporter protein as described herein. In some embodiments, the reporter protein to be used is one that facilitates in vivo detection (e.g., imaging) of the introduced cells. For example, the cells may express a far-red emitting fluorescent protein such as Katushka, whose long excitation and emission wavelengths are well suited to imaging in tissues. Katushka is commercially available under the tradename "TurboFP635" (Evrogen, Moscow, Russia),

EXAMPLE

While the disclosure has been particularly shown and described with reference to specific embodiments (some of which are preferred embodiments), it should be understood by those having skill in the art that various changes in form and detail may be made therein without departing from the spirit and scope of the present disclosure as disclosed herein.

Example 1

This example illustrates the expression level of HLA-F in iPS (iPSC 9211) and HEK-293 cells with or without transfection of exogenous nucleic acid.

To measure the mRNA level of HLA-E, HLA-F and HLA-G in the cells, total RNA was extracted from the cells using Quick-RNA Microprep Kit (Zymo Research). cDNA was prepared from the total RNA extraction using iScript cDNA Synthesis Kit (Bio-Rad). The level of HLA-E, F and G was assayed by real time PCR using go-Tag green polymerase (Promega) with the following primers.

TABLE 1

Primers for detecting HLA-E, F and G.

| Primer | Sequence | SEQ ID NO |
|---|---|---|
| HuHLA-E-F | TTCGCCTACGACGGCAAGGA | 32 |
| HuHLA-E-R | CCCTTCTCCAGGTATTTGTG | 33 |
| HuHLA-F-F | GGCAGAGGAATATGCAGAGGAGTT | 34 |
| HuHLA-F-R | CTCTGTGTCCTGGGTCTGTTC | 35 |
| HuHLA-G-F | TTGGGAAGAGGAGACACGGAACA | 36 |
| HuHLA-G-R | AGGTCGCAGCCAATCATCCAC | 37 |
| XC423-HLA-G-F-1 | GAGCGAGGCCAGTGAGTAA | 38 |
| XC424-HLA-G-R-1 | TCTCCCAGGTAGAGGGTCTG | 39 |
| XC425-HLA-G-F-2 | GCCTCCCTGATCTCCTGTAG | 40 |
| XC426-HLA-G-R-2 | GACGGACCCTCAGAATCACT | 41 |
| XC427-HLA-E-F-1 | CTCCGAGCAAAAGTCAAATG | 42 |
| XC428-HLA-E-R-1 | CCTAGCCCAAGAAGGAGATG | 43 |
| XC429-HLA-E-F-2 | TAAGTCCAGGCTGGTGTCAA | 44 |

The qRT-PCR results for assaying mRNA level of HLA-E, F and G in iPS cells are shown in Table 2 below.

TABLE 2

HLA-E, F and G expression in iPSC lines.

| | | Fold difference in mRNA level to control | | | |
|---|---|---|---|---|---|
| Taget | Cells | Experiment #1 | Experiment #2 | Experiment #3 | Experiment #4 |
| HLA-E | 9211-1 | 23 | 14 | 27 | 5 |
| | 9211-2 | 7 | 6 | 29 | 3 |
| | 9211-Diff (20 d) | | 29 | 62 | 13 |
| | PBMC | 917 | 906 | 2196 | 616 |

TABLE 2-continued

HLA-E, F and G expression in iPSC lines.

| Taget | Cells | Fold difference in mRNA level to control | | | |
|---|---|---|---|---|---|
| | | Experiment #1 | Experiment #2 | Experiment #3 | Experiment #4 |
| HILA-F | 9211-1 | 1 | 89 | 257 | 37 |
| | 9211-2 | 1 | 93 | 217 | 35 |
| | 9211-Diff (20 d) | | 8 | 1 | 1 |
| | PBMC | 1068 | 347 | 1559 | 2695 |
| HLA-G | 9211-1 | 358 | 1 | 4 | 468 |
| | 9211-2 | 147 | 0 | 2 | 592 |
| | 9211-Diff (20 d) | | 11 | 45 | 347 |
| | PBMC | 1206 | 919 | 1894 | 7128 |

Example 2

This example illustrates the expression of HLA-F in modified and unmodified HEK293 cells.

The inventors had previously made the TARGATT™ HEK293 cells ready for gene insertion (see FIG. 7). Using the TARGATT™ HEK293 cells, the inventors generated modified HEK293 cells that contain a single copy insertion of HLA-F or HLA-G at the safe harbor genomic H11 locus. The same qRT-PCR was performed to measure mRNA expression. The data in Table 3 shows that HEK293 cells have higher basal level HLA expression compared to iPS cells, with HLA-F and G being expressed much higher than HLA-E in HEK293. One copy of exogenous HLA-F and HLA-G increased HLA-F and HLA-G expression by 10-fold and 7-fold, respectively.

TABLE 3

HLA-E, F and G expression in modified or unmodified HEK293 cells. iPSC was included in the same experiment for comparison purposes.

| | Cell | Fold difference in mRNA |
|---|---|---|
| HLA-E | 9211-1 | 5 |
| | 9211-2 | 3 |
| | 9211-differentiated | 13 |
| | HEK | 102 |
| | HEK-HLA-F | 37 |
| | HEK-HLA-G | 47 |
| | PBMC | 616 |
| HLA-F | 9211-1 | 37 |
| | 9211-2 | 35 |
| | 9211-differentiated | 1 |
| | HEK | 3393 |
| | HEK-HLA-F | 33865 |
| | HEK-HLA-G | 1565 |
| | PBMC | 2695 |
| HLA-G | 9211-1 | 468 |
| | 9211-2 | 592 |
| | 9211-differentiated | 347 |
| | HEK | 22011 |
| | HEK-HLA-F | 5682 |
| | HEK-HLA-G | 148496 |
| | PBMC | 7128 |

Example 3

This example illustrates the expression of HLA-F variants in HEK293 cells.

A naturally occurring HLA-F comprises from N-terminus to C-terminus: an HLA-F alpha 1 domain, an alpha 2 domain, an alpha 3 domain, a transmembrane domain and a cytoplasmic domain. The HLA-F alpha 1 domain and alpha 2 domain form the groove of peptide binding. The HLA-F alpha 3 domain associates with beta-2 microglobin (β2M), which is necessary for the stability of HLA-F complex.

Besides the "canonical" isoform 1 with 346 amino acids (SEQ ID NO: 1 or 2) (designated as "HLA-F-S" for HLA-F short form in Tables 4), HLA-F exists in several isoforms, mainly isoform 3, which is the longest isoform with an extra 96 amino acid sequence in its cytoplasmic region (designated as "HLA-F-L" for HLA-F long form, SEQ ID NO: 3 or 4).

Figure 5C:
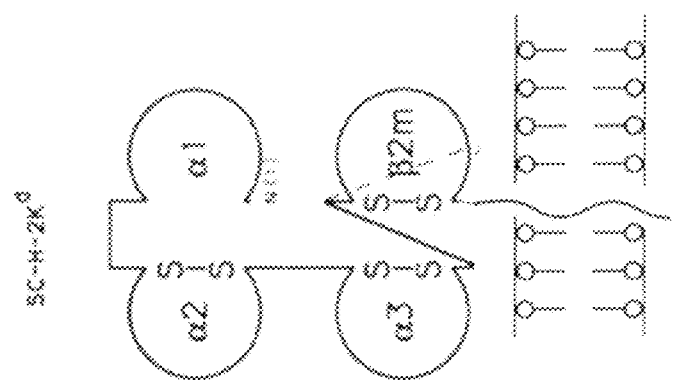
FIGS. 5A, 5B and 5C are schematics of the structures of HLA-F-β2m fusion proteins.
Figure 5B:
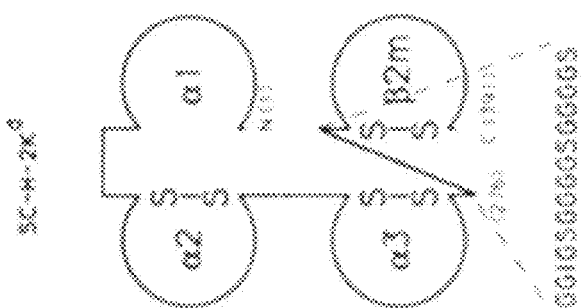
Figure 5A:
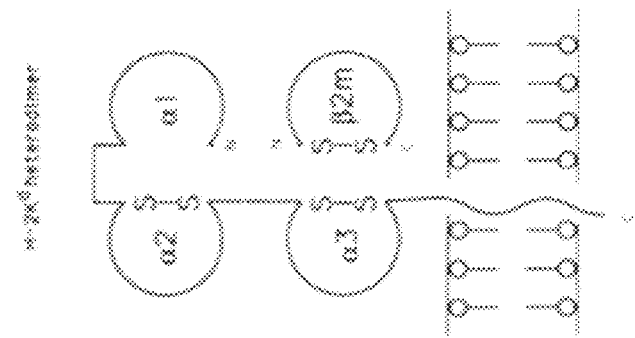

The inventors generated a HLA-F-β2M fusion (FIG. 5C), which contains from N to C terminus, a signal peptide, alpha1, 2 and 3 domains, 15-amino acid $(GGGGS)_3$ linker, β2M, transmembrane and cytoplasmic domain. The inventors generated HEK293 cells contain the fusion either in HLA-F short or long form.

Data in Table 4 shows that (i) One copy of exogenous gene insertion increased HLA-F and HLA-F-β2M mRNA expression level by over 100-fold in HEK293 cells; (ii) mRNA expression level is similar for all three HLA-F variants tested. The higher gene expression level in this round of experiments compared to Table 3 data is probably due to the different promoters used in the two experiments. Table 3 experiment used CAG promoter, whereas Table 4 used CEF (CHO EF1 alpha) promotor.

TABLE 4

Expression of HLA-E, F and G in modified HEK293 cells.

| | Cells | Fold difference in mRNA |
|---|---|---|
| HLA-E | iPSC (ASE9-9211) | 3 |
| | HEK-HLA-F-S | 18 |
| | HEK-HLA-F-S-β2M | 23 |
| | HEK-HLA-F-S-β2M | 11 |
| | PBMC | 616 |
| HLA-F | iPSC (ASE9-9211) | 104 |
| | HEK-HLA-F-S | 251998 |
| | HEK-HLA-F-S-β2M | 389922 |
| | HEK-HLA-F-S-β2M | 243664 |
| | PBMC | 2695 |
| HLA-G | iPSC (ASE9-9211) | 780 |
| | HEK-HLA-F-S | 8508 |
| | HEK-HLA-F-S-β2M | 7776 |
| | HEK-HLA-F-S-β2M | 8225 |
| | PBMC | 7128 |

Example 4

This example illustrates that the expression of exogenous HLA-F protein reduces immunogenicity of HEK-293 cells in a NK cytotoxicity assay.

To perform cytotoxicity assay, $5 \times 10^4$ HEK-293 cells detached using EDTA were co-cultured with $2.5 \times 10^6$ PBMC cells for 4 hours. The cells were then collected, washed 2 times in PBS, and stained with Green Dye (Thermo Fisher L23101) for 30 mins in 4° C. with light protection. Afterwards, the cells were spun down, washed 2 times in 2% FBS+PBS, and subjected to FACS analysis. Three groups of cells were used in the assay: HEK293 cells expressing control mCherry gene; HEK293 cells expressing HLA-G gene regulated by CEF promoter, CHO EF1 alpha promoter (CEF-HLA-G) (Zhao et al. 2014; Hantash 2017); HEK293 cells expressing HLA-F-β2M fusion gene regulated by CEF promoter (CEF-HLA-F-β2M). As shown in FIG. 6 and Table 5 from 3 independent experiments, expression of exogenous HLA-G and HLA-F-β2M protein significantly reduced NK cell mediated cytotoxicity, with HLA-G being slightly more effective than HLA-F. The inventors decided to use HLA-F long form fusion because the long form fusion had given more consistent immune protection result than the short form fusion.

TABLE 5

Exogenous expression of HLA-G and HLA-F-β2M protein reduce NK cell mediated cytotoxicity

|  | Cell Death Ratio | | | | Standard Error |
|---|---|---|---|---|---|
|  | Exp # 1 | Exp # 2 | Exp # 3 | Average | |
| mCherry HEK | 1.000 | 1.000 | 1.000 | 1.000 | 0.000 |
| CEF-HLA-G | 0.719 | 0.768 | 0.711 | 0.733 | 0.025 |
| CEF-HLA-F-β2M | 0.762 | 0.873 | 0.752 | 0.795 | 0.055 |

Example 5

This example illustrates the generation of iPSC lines expressing HLA-F-β2M fusion, and HLA-F.

HLA-F peptide-bound form specifically interacts with inhibitory NK cell receptors, thus rendering cells with a "missing self" signal. The inventors showed in Example 4 that expressing an HLA-F-β2M fusion protein in HEK293 cells were more resistant to killing by NK cells. Modified iPS cells containing HLA-F-β2M are generated in order to test for their immune protection activities. The results show that genetically modified iPS cells expressing exogenous HLA-F-β2M protein have reduced immunogenicity relative to corresponding mammalian cells that do not express the exogenous HLA-F-β2M.

The inventors established a TARGATT™ master iPSC line that contains a landing pad (attP) at the H11 safe harbor locus. This cell line is used to insert the HLA genes using TARGATT™ technology (FIG. 7), each containing HLA-F, and HLA-F-β2M, respectively. Briefly, the HLA gene is cloned into a donor plasmid AST-3070 at the MCS (multiple cloning site), and then co-transfected with plasmid AST-3071 (containing phiC31 integrase) into the TARGATT master iPS cells. PhiC31 catalyzes recombination between the attP and attB site, resulting in an integration of the HLA gene at the landing pad. Any non-integrants, random or non-specific gene insertion are eliminated by adding hygromycin and ganciclovir which kills cells that express thymidine kinase (TK), as a negative selection marker. Positive clones are selected first with hygromycin and then enriched with ganciclovir selection. The results showed 46% efficiency with hygromycin selection, and 67% with hygromycin and ganciclovir selection in site-specific gene insertion using this system (FIGS. 8A, 8B and 8C). The inventors use qRT-PCR to assay the HLA mRNA level in these modified iPS cells using the same method described above in Example 1. The inventors also perform Western Blots and immunostaining to assay HLA protein distribution (cytoplasmic vs. cell surface) and expression in cells.

Example 6

This example illustrates the development of the assays for examining immune-protection activity in cell lines generated in Example 5.

The data in HEK293 cells has shown decreased NK cell killing in cells expressing HLA-F-β2M.

NK-Mediated Cytotoxicity Assay

An NK cytotoxicity assay is developed based on the specific culture conditions for iPS cells. In comparison to HEK293 cells, iPS cells require more growth factors, and regular iPSC culture conditions usually contain unknow ingredients or animal ingredients. For example, Matrigel is routinely used for coating culture dishes for iPSC culture. These unknown components and growth factors can potentially interfere with NK based cytotoxicity assay. The inventors use defined and animal ingredient free reagents and media to culture iPS cells. The inventors use Vitronectin, which is a recombinant human protein to coat culture plates and TeSR-ACF media (Stem Cell Technologies) to culture iPS cells. NK cytotoxicity assay is carried out using two sources of NK cells: one is commercially purchased NK cells (ReachBio) and the other is produced by the inventors, which is iNK cells differentiated from iPS cells. The assay is done using the LIVE/DEAD® Cell-Mediated Cytotoxicity Kit (Molecular probe, L7010) (ThermoFisher). Briefly, NK cells activated by IL2 (effector cells) are mixed with target cells (iPSC and its differentiated cells in single cell suspension) at a ratio of 1:1, 2:1, 4:1, and 10:1 and incubate for 4 hours at 37° C. in a humidified 5% $CO_2$ incubator. Live/dead cells are determined by FACS analysis according to manufacturer's instruction. Each assay condition is done in triplicates. The results show that iPSCs with HLA-F and HLA-G expression have less cell lysis compared to wildtype iPSC.

Mixed T Lymphocyte Reaction (MLR) Assay

The inventors perform MLR assay to determine T lymphocyte proliferation when mixing with HLA expressing and control iPS cells. Human peripheral blood mononuclear cells (PBMCs) are purchased from San Diego Blood Bank (additional sources include HemaCare, Stem Cell Technologies) and thawed according to the manufacturer's protocol and immediately used in the assays. Proliferation of human peripheral blood mixed T lymphocytes is measured using CellTrace CFSE Cell Proliferation Kit (ThermoFisher). Briefly, PBMCs are labeled with CFSE, and iPSCs are treated with Mitomycin C (Sigma-Aldrich) to inactivate cell division. Treated iPS cells are dissociated to single cell suspensions and seeded at $1 \times 10^5$ per well in 96-well plates. The same number of human CFSE-labeled PBMCs in 50 μl will be added to the 96-well plates. The cell mixture will be incubated at 37° C. for 24 hours and then subject to flow cytometry analysis. T cell proliferation is determined by CFSE signal, and fluorescence is normalized with autofluorescence from iPS cells. Each assay is performed in triplicate. The results show the inhibitory effect in T cell proliferation from the iPS cells expressing HLA-F-β2M and HLA-G.

Immune Characteristics of iPSC Differentiated Cells

The cells that are eventually used for allograft transplantation are iPSC differentiated cells. It is therefore important to test immune activities of differentiated cells. iPSCs are differentiated to the following cell types for this purpose, including neural progenitor cells (NPC), pancreatic precursor cells (PPC), and hematopoietic progenitor cells (HPC). These 3 types of cells are chosen because each represents a germinal layer type of cells. Also, the inventors already developed iPSC differentiation protocols for these cell types. iPSC expressing HLA-G or HLA-F-β2M are differentiated into NPCs, PPC and HPCs using the inventors' established protocols. Differentiated cells are subjected to cytotoxicity and MLR assays.

The results show that iPSC and its differentiated cells expressing HLA-F-β2M have reduced immunogenicity compared to cells without HLA-F-β2M.

Example 7

This example illustrates the generation of universal iPSC expressing a combination of HLA-G-β2M, HLA-F-β2M, and CD95L.

Expression of exogenous HLA-G was shown to decrease immunogenicity of human ES cell and their epidermal derivatives (Zhao et al. 2014). HLA-G, like HLA-F, exerts its immunomodulatory functions through the interaction with multiple receptors such as LILRB1 (ILT2/CD85j), LILRB2 (ILT4/CD85d), and KIR2DL4 (CD158d), which are differentially expressed by immune cells. The interaction of HLA-G molecules with inhibitory receptors induces apoptosis of activated CD8+ T cells (Kapasi et al. 2000), modulates the activity of NK cells (Rajagopalan and Long 1999) and dendritic cells (DC) (Liang et al. 2008). Interaction of LILRB1 with its ligand, for example causes phosphorylation of its immunoreceptor tyrosine-based inhibitory motifs (ITIMS) that initiate the inhibitory cascade. This interaction occurs with the α3-domain and β2M (Brown et al. 2004). In fact, β2M free HLA-G molecules are not recognized by LILRB1. To improve the NK inhibitory pathway, the inventors express a fusion of HLA-G-β2M, similar to HLA-F-β2M to get better immune protection in donor cells than HLA-G alone. The inventors generate iPSC donor cells that co-express HLA-G-β2M and HLA-F-β2M to enhance HLA interaction with multiple NK inhibitory receptors (Lin and Yan 2019; Alegre et al. 2014). The inventors chose HLA-G instead of HLA-E or both because HLA-G and HLA-E in some cases act on overlapping NK inhibitory receptors (Gornalusse et al. 2017). The inventors further express CD95L as an additional immune cloaking strategy. CD95 (FAS), a cell surface protein, can mediate apoptosis when bound to its natural ligand, CD95L(FASL) or stimulated with agonistic antibodies (Peter et al. 2015). It is ubiquitously expressed in the body, but is particularly abundant in the thymus, liver, heart, and kidney. CD95L is predominantly expressed in activated T lymphocytes and natural killer cells and is constitutively expressed in tissues of "immune-privilege sites" such as the testis and eye, suggesting its function in immune protection. The results show that co-expressing HLA-G, F, and CD95L blocks both NK and T cell-mediated allograft rejection.

Construct design: The inventors construct three iPSC lines: 1) line one contains HLA-F-β2M; 2) line two contains (HLA-F-β2M)-2A-(HLA-G-β2M); 3) line 3 contains (HLA-G-β2M)-2A-(HLA-F-β2M)-2A-CD95L (FIG. 9). These lines are generated using the TARGATT™ gene insertion technology. Briefly, donor plasmid containing the immune transgene cassette and landing pad Bxb1 attP (recognized by Bxb1 integrase, orange arrowheads) are inserted using phiC31 integrase through recombination between pseudo attP sites in the iPSC genome and C31 attB (recognized by phiC31 integrase) on the donor plasmid. The modified locus contains the immune gene cassette and reporter cassette flanked by Bxb 1 integrase recognition sites, Bxb 1 attP. The reporter cassette is "swapped" out with any gene of interest using Bxb 1 integrase, whereas Cre recombination removes the green reporter cassette. This design makes it easy to insert any genes of interest in the TARGATT™ universal iPSC line.

Generate modified iPSC line: To select an iPSC line that can be potentially used for clinical use, the inventors use the NHCDR-000750 line which was originally derived in the NIH. It is a research grade line that matches the cGMP line NHCDR-000740. This makes transition to clinical grade cells a straightforward process.

Example 8

This example illustrates the characterization of immunogenicity of the universal master iPSC and its differentiated cells.

Genomic analysis of modified iPS cells: TARGATT gene insertion technology has shown very low off target events compared to other gene editing methods such as CRISPR/Cas9. The inventors carry out PCR and next generation sequencing to analyze the transgene containing clones and ensure only the desired insertion are present in the modified cells. Whole genome sequencing (WGS) is also performed to rule out any DNA damage in the iPS geneome.

In vitro cytotoxicity and immune assay: NK cytotoxicity assay and MLR assay are performed as described above in Example 4.

In vivo reactivity with allogeneic CD8+ T cells: The in vivo reactivity assay is a teratoma-based assay, in which iPSCs are differentiated in immunodeficient mice to all 3 germinal layer cells to form teratoma.

Immunodeficient mice, NSG mice, are purchased from the Jackson Laboratory (Bar Harbor, MN). Non-modified iPSC (wildtype), and each of the 3 modified iPSC line, at 1 million cells/inoculation site, are injected subcutaneously into 5 NSG mice per line. Allogeneic human CD8+ T cells ($8.5 \times 10^5$) are activated and injected intravenously into each mouse via retro-orbital sinus on day 35 after iPSC implantation. Harvested teratomas (at day 56) are measured by weight and size, as well as analyzed by hematoxylin and eosin (H&E) staining of paraffin-embedded sections. Anti-human CD8 antibody staining of frozen sections allow semi quantitative analysis of CD8+ T cell infiltration in histological sections. The results show that teratoma formed from the iPSC expressing all 3 transgenes is the most resistant to infiltration or lysis by CD8+ T cells.

The universal donor cells generated in this proposal leave the endogenous HLA genes un-touched, therefore maintaining the endogenous immune defense homeostasis against tumorigenesis or viral infection. This is superior in safety to other universal cells in which the HLA-class 1 genes are knocked-out (Gornalusse et al. 2017). Absent or reduced HLA expression helps tumor cells evade immune responses (Hicklin et al. 1998). If malignant transformation of a transplanted HLA-negative cell occurred, it would be harder to eliminate through normal immune mechanisms. Therefore, it is especially important that transplanted cell populations are screened for oncogenic mutations.

Example 9

This example illustrates the development of a therapeutic CAR-iNK product using the universal iPSC platform.

Natural Killer (NK) cells and CD8+ cytotoxic T cells are two types of immune cells that can kill target cells through similar cytotoxic mechanisms. Anti-CD19 chimeric antigen receptor (CAR) T-cell therapy has shown remarkable clinical efficacy in B-cell cancers. However, CAR-T cells can induce substantial toxic effects, and the manufacture of the cells is complex. Compared to CAR-T cells, CAR-NK cells could offer some significant advantages, including: 1) better safety, such as a lack or minimal cytokine release syndrome and neurotoxicity in autologous setting (Chou and Turtle 2019) and graft-versus-host disease in allogenic setting (Lupo and Matoseyic 2019), 2) multiple mechanisms for activating cytotoxic activity, and 3) high feasibility for 'off-the-shelf' manufacturing. CAR-NK cells could be engineered to target diverse antigens, enhance proliferation and persistence in vivo, increase infiltration into solid tumors, overcome resistant tumor microenvironment, and ultimately achieve an effective anti-tumor response. In fact, Liu et al. (2020) reported their Phase I/II study using CD19-CAR-NK cells to treat CD19+ lymphoma and observed positive clinical results both in safe and efficacy. The administration of CAR-NK cells was not associated with the development of cytokine release syndrome, neurotoxicity, or graft-versus-host disease, and there was no increase in the levels of inflammatory cytokines, including interleukin-6, over baseline. Of the 11 patients who were treated, 8 (73%) had a response; of these patients, 7 (4 with lymphoma and 3 with CLL) had a complete remission, and 1 had remission of the Richter's transformation component but had persistent CLL. Responses were rapid and seen within 30 days after infusion at all dose levels. The infused CAR-NK cells expanded and persisted at low levels for at least 12 months.

Engineer iPSC expressing CD19CAR and IL15: the inventors express CD19-CAR together with IL-15 in the UM-iPSC and then differentiate to NK cells to produce CD19CAR-iNK. IL-15 has been shown to enhance NK cell survival and expansion in vivo (Hermanson et al. 2016).

Using the universal iPS master cells, the inventors insert CD19-CAR and IL-15 using the Bxb1 integrase (FIG. 10). With integrase Bxb1, attB sites on the donor plasmid containing the CD19CAR-IL15 cassette recombine with the attP sites in the iPSC genomic locus. This results in replacement of the reporter cassette (green box) with the CD19CAR-IL15 cassette. The "*" in attB* and attP* indicates different core sequences from that of attB and attP to control recombination direction, such that only the transgene is recombined into the genome, but not the plasmid backbone. The engineered iPSCs are then differentiated to NK cells, which is further purified by FACS sorting to reach over 95% purity.

In vitro function of CAR-iNK: To assess NK cytotoxicity, the inventors compare in vitro potential of CAR-iNKs_vs. iNK without CAR to kill Raji and NALM-6 (ATCC) CD19+ cancer cell lines at multiple E:T ratios by using the LIVE/DEAD® Cell-Mediated Cytotoxicity Kit (Molecular probe, L7010) (ThermoFisher) and methods disclosed in Example 6. The results show that CAR-iNKs have a higher killing potential against Raji and NALM-6 CD19+ cell lines than non-modified NK cells. To further address the specific killing ability of CD19-CAR-iNK cells, K562 cells expressing CD19 (K562/CD19) and parental K562 cells (CD19 negative) are used as target cells. The same cytotoxicity assay is carried out. The results show that CD19-CAR-iNK cells lyse $CD19^+$ cells more effectively than $CD19^-$ cells.

Preclinical animal model study: The inventors generate Raji xenograft models to test CAR-iNK in targeting tumor. Raji is the first hematopoietic human cell line isolated from an 11-year-old black male patient with Burkitt's lymphoma and an excellent transfection host for a variety of molecular biology applications. Raji B-cell lymphoma model is well established for CD19-CAR cell therapy (Tsukahara et al. 2013). To test for accumulation of CAR-iNK at the tumor sites, 10-12-week old NSG mice (the Jackson Laboratory, Bar Harbor, ME) are injected subcutaneously with $5 \times 10^6$ Raji cells transduced with luciferase reporter (Raji/Luc cells). Two weeks after inoculation, $10^7$ CD19-CAR-iNK cells are injected intravenously into tumor bearing mice. Tumors are removed 24 hours after iNK cell infusion and analyzed by immunohistochemistry using anti-CD56 antibody.

To further evaluate the anti-tumor effects of CAR-iNK, NSG mice are injected intravenously with $5 \times 10^4$ Raji/Luc cells on day 0, and are then adoptively transferred with a single intravenous infusion of $10^7$ CD19-CAR-iNK cells or control non-modified iNK cells on day 3. To monitor the progression of Raji/Luc cells in vivo, the substrate of luciferase, D-luciferin are injected intraperitoneally into the mice (75 mg/kg body weight), and bioluminescence imaging is done at days 15, 21 and 29 using an IVIS imaging system with Living Image software (Xenogen, Hopkinton, MA). The following data are analyzed including animal survival, cytokine levels (such as IFN-γ and GM-CSF, IL-1a, IL-1Ra, IL-2, IL-2Ra, IL-6, etc.), GVHD, immunohistochemical staining for human CD56 in the spleen, lesions from tumor bearing mice at day 29 after iNK cell administration. All mouse experiments are carried out in a humane manner after receiving approval from the OUHSC (The University of Oklahoma Health Sciences Center) Institutional Animal Care & Use Committee (IACUC) where the animal facility is located.

The results show that the engineered CD19CAR-iNKs are safe and efficacious in animal models, with no or minimal GVHD, cytokine release syndrome or neurotoxicity often caused by CD19-CAR-T cells.

Example 10

This example illustrates that overexpression of HLA-F has immune-repression activity in iPSCs. Similar NK-mediated toxicity assays as in Example 4 were performed using iPSC that express HLA-F-β2M (HLA-FB) except that CD56+NK cells were used as effector cells instead of PBMC. Data from one such experiment is shown in FIG. 11. Several ratios, including 1:1, 2:1 and 4:1 of effector (NK cells) versus target cells (iPSC) were used. Each group contain 3 samples. The ratio of effector:target=2:1 showed lower cell death of 39% from 59% with a "p" value of 0.0231, indicating statistically significant immune protection from HLA-FB expression.

The invention claimed is:

1. A genetically modified mammalian cell comprising an exogenous nucleic acid encoding an HLA-F protein expressed on the surface of the genetically modified mammalian cell, wherein the genetically modified mammalian cell has reduced immunogenicity and/or improved immunosuppression as compared to a mammalian cell of the same-type without said exogenous nucleic acid, wherein the HLA-F protein is a chimeric HLA-F protein comprising, from N-terminus to C-terminus,
- an extracellular region comprising an HLA-F alpha 1 domain, an HLA-F alpha 2 domain, an HLA-F alpha 3 domain, a linker and a beta-2 microglobulin (β2m) protein,
- a transmembrane domain, and
- an intracellular domain.

2. The genetically modified mammalian cell of claim 1, wherein the extracellular region of the chimeric HLA-F protein has an amino acid sequence of SEQ ID NO: 20 or 21.

3. The genetically modified mammalian cell of claim 1, which is modified from a cell selected from the group consisting of: a human cell, an embryonic stem cell or iPS cell, a cell differentiated from a stem/progenitor cell, a T cell and a NK cell.

4. The genetically modified mammalian cell of claim 1, further comprising an exogenous nucleic acid encoding an HLA-G and/or an exogenous nucleic acid encoding CD95L, wherein the HLA-G protein comprises an extracellular region which comprises an HLA-G alpha 1 domain, an HLA-G alpha 2 domain, an HLA-G alpha 3 domain and a beta-2 microglobulin (β2m) protein.

5. The genetically modified mammalian cell of claim 1, further comprising a chimeric antigen receptor (CAR).

6. The genetically modified mammalian cell of claim 5, wherein the CAR is an anti-CD19 CAR.

7. The genetically modified mammalian cell of claim 1, wherein the HLA-F protein is expressed by the genetically modified mammalian cell for at least 5 weeks.

8. The genetically modified mammalian cell of claim 1, wherein the reduced immunogenicity and/or improved immunosuppression of the genetically modified mammalian cell as compared to the mammalian cell without said exogenous nucleic acid is determined by a NK cell cytotoxicity assay.

* * * * *

SEQUENCE LISTING

```
Sequence total quantity: 44
SEQ ID NO: 1            moltype = AA  length = 346
FEATURE                 Location/Qualifiers
source                  1..346
                        mol_type = protein
                        organism = Homo sapiens
SEQUENCE: 1
MAPRSLLLLL SGALALTDTW AGSHSLRYFS TAVSRPGRGE PRYIAVEYVD DTQFLRFDSD    60
AAIPRMEPRE PWVEQEGPQY WETTGYAKA NAQTDRVALR NLLRRYNQSE AGSHTLQGMN    120
GCDMGPDGRL LRGYHQHAYD GKDYISLNED LRSWTAADTV AQITQRFYEA EEYAEEFRTY   180
LEGECLELLR RYLENGKETL QRADPPKAHV AHHPISDHEA TLRCWALGFY PAEITLTWQR   240
DGEEQTQDTE LVETRPAGDG TFQKWAAVVV PPGEEQRYTC HVQHEGLPQP LILRWEQSPQ   300
PTIPIVGIVA GLVVLGAVVT GAVVAAVMWR KKSSDRNRGS YSQAAV                 346
```

```
SEQ ID NO: 2            moltype = AA  length = 346
FEATURE                 Location/Qualifiers
source                  1..346
                        mol_type = protein
                        organism = Homo sapiens
SEQUENCE: 2
MAPRSLLLLL SGALALTDTW AGSHSLRYFS TAVSRPGRGE PRYIAVEYVD DTQFLRFDSD    60
AAIPRMEPRE PWVEQEGPQY WEWTTGYAKA NAQTDRVALR NLLRRYNQSE AGSHTLQGMN   120
GCDMGPDGRL LRGYHQHAYD GKDYISLNED LRSWTAADTV AQITQRFYEA EEYAEEFRTY   180
LEGECLELLR RYLENGKETL QRADPPKAHV AHHPISDHEA TLRCWALGFY PAEITLTWQR   240
DGEEQTQDTE LVETRPAGDG TFQKWAAVVV PSGEEQRYTC HVQHEGLPQP LILRWEQSPQ   300
PTIPIVGIVA GLVVLGAVVT GAVVAAVMWR KKSSDRNRGS YSQAAV                 346

SEQ ID NO: 3            moltype = AA  length = 442
FEATURE                 Location/Qualifiers
source                  1..442
                        mol_type = protein
                        organism = Homo sapiens
SEQUENCE: 3
MAPRSLLLLL SGALALTDTW AGSHSLRYFS TAVSRPGRGE PRYIAVEYVD DTQFLRFDSD    60
AAIPRMEPRE PWVEQEGPQY WEWTTGYAKA NAQTDRVALR NLLRRYNQSE AGSHTLQGMN   120
GCDMGPDGRL LRGYHQHAYD GKDYISLNED LRSWTAADTV AQITQRFYEA EEYAEEFRTY   180
LEGECLELLR RYLENGKETL QRADPPKAHV AHHPISDHEA TLRCWALGFY PAEITLTWQR   240
DGEEQTQDTE LVETRPAGDG TFQKWAAVVV PPGEEQRYTC HVQHEGLPQP LILRWEQSPQ   300
PTIPIVGIVA GLVVLGAVVT GAVVAAVMWR KKSSDRNRGS YSQAAAYSVV SGNLMITWWS   360
SLFLLGVLFQ GYLGCLRSHS VLGRRKVGDM WILFFLWLWT SFNTAFLALQ SLRFGFGFRR   420
GRSFLLRSWH HLMKRVQIKI FD                                           442

SEQ ID NO: 4            moltype = AA  length = 442
FEATURE                 Location/Qualifiers
source                  1..442
                        mol_type = protein
                        organism = Homo sapiens
SEQUENCE: 4
MAPRSLLLLL SGALALTDTW AGSHSLRYFS TAVSRPGRGE PRYIAVEYVD DTQFLRFDSD    60
AAIPRMEPRE PWVEQEGPQY WEWTTGYAKA NAQTDRVALR NLLRRYNQSE AGSHTLQGMN   120
GCDMGPDGRL LRGYHQHAYD GKDYISLNED LRSWTAADTV AQITQRFYEA EEYAEEFRTY   180
LEGECLELLR RYLENGKETL QRADPPKAHV AHHPISDHEA TLRCWALGFY PAEITLTWQR   240
DGEEQTQDTE LVETRPAGDG TFQKWAAVVV PSGEEQRYTC HVQHEGLPQP LILRWEQSPQ   300
PTIPIVGIVA GLVVLGAVVT GAVVAAVMWR KKSSDRNRGS YSQAAAYSVV SGNLMITWWS   360
SLFLLGVLFQ GYLGCLRSHS VLGRRKVGDM WILFFLWLWT SFNTAFLALQ SLRFGFGFRR   420
GRSFLLRSWH HLMKRVQIKI FD                                           442

SEQ ID NO: 5            moltype = DNA  length = 1329
FEATURE                 Location/Qualifiers
source                  1..1329
                        mol_type = genomic DNA
                        organism = Homo sapiens
SEQUENCE: 5
atggcgcccc gaagcctcct cctgctgctc tcaggggccc tggccctgac cgatacttgg    60
gcaggctccc actccttgag gtatttcagc accgctgtgt cgcggcccgg ccgcggggag   120
ccccgctaca tcgccgtgga gtacgtagac gacacgcaat tcctgcggtt cgacagcgac   180
gccgcgattc cgaggatgga gccgcggag ccgtgggtgg agcaagaggg gccgcagtat   240
tgggagtgga ccacagggta cgccaaggcc aacgcacaga ctgaccgagt ggccctgagg   300
aacctgctcc gccgctacaa ccagagcgag gctgggtctc acaccctcca gggaatgaat   360
ggctgcgaca tggggcccga cggacgcctc ctccgcgggt atcaccagca cgcgtacgac   420
ggcaaggatt acatctccct gaacgaggac ctgcgctcct ggaccgcggc ggacaccgtg   480
gctcagatca cccagcgctt ctatgaggca gaggaatatg cagaggagtt caggacctac   540
ctggagggcg agtgcctgga gttgctccgc agatacttgg agaatgggaa ggagacgcta   600
cagcgcgcag atcctccaaa ggcacacgtt gcccaccacc ccatctctga ccatgaggcc   660
accctgaggt gctgggccct gggcttctac cctgcggaga tcacgctgac ctggcagcgg   720
gatgggagg aacagaccca ggacacagag cttgtggaga ccaggcctgc aggggatgga   780
accttccaga agtggccgc tgtggtggtg ccttctggag aggaacagag atacacctgc   840
catgtgcagc acgaggggct gccccagccc ctcatcctga tgggagca gtctcccag    900
cccaccatcc ccatcgtggg catcgttgct ggccttgttg tccttggagc ctgtggtcact   960
ggagctgtgg tcgctgctgt gatgtggagg aagaagagct cagatagaaa cagagggagc  1020
tactctcagg ctgcagccta ctcagtggtc agcggaaact tgatgataac atggtggtca  1080
agcttatttc tcctgggggt gctcttccaa ggatatttgg gctgcctccg gagtcacagt  1140
gtcttgggcc gccggaaggt gggtgacatg tggatcttgt ttttttttgtg gctgtggaca  1200
tctttcaaca ctgccttctt ggccttgcaa agccttcgct ttggcttcgg ctttaggagg  1260
ggcaggagct tccttcttcg ttccttggcac catcttatga aagggtccaa gattaagatt  1320
tttgactga                                                         1329

SEQ ID NO: 6            moltype = AA  length = 305
FEATURE                 Location/Qualifiers
source                  1..305
                        mol_type = protein
                        organism = Homo sapiens
```

```
SEQUENCE: 6
MAPRSLLLLL SGALALTDTW AGSHSLRYFS TAVSRPGRGE PRYIAVEYVD DTQFLRFDSD    60
AAIPRMEPRE PWVEQEGPQY WEWTTGYAKA NAQTDRVALR NLLRRYNQSE AGSHTLQGMN   120
GCDMGPDGRL LRGYHQHAYD GKDYISLNED LRSWTAADTV AQITQRFYEA EEYAEEFRTY   180
LEGECLELLR RYLENGKETL QRADPPKAHV AHHPISDHEA TLRCWALGFY PAEITLTWQR   240
DGEEQTQDTE LVETRPAGDG TFQKWAAVVV PPGEEQRYTC HVQHEGLPQP LILRWEQSPQ   300
PTIPI                                                              305

SEQ ID NO: 7            moltype = AA   length = 305
FEATURE                 Location/Qualifiers
source                  1..305
                        mol_type = protein
                        organism = Homo sapiens
SEQUENCE: 7
MAPRSLLLLL SGALALTDTW AGSHSLRYFS TAVSRPGRGE PRYIAVEYVD DTQFLRFDSD    60
AAIPRMEPRE PWVEQEGPQY WEWTTGYAKA NAQTDRVALR NLLRRYNQSE AGSHTLQGMN   120
GCDMGPDGRL LRGYHQHAYD GKDYISLNED LRSWTAADTV AQITQRFYEA EEYAEEFRTY   180
LEGECLELLR RYLENGKETL QRADPPKAHV AHHPISDHEA TLRCWALGFY PAEITLTWQR   240
DGEEQTQDTE LVETRPAGDG TFQKWAAVVV PSGEEQRYTC HVQHEGLPQP LILRWEQSPQ   300
PTIPI                                                              305

SEQ ID NO: 8            moltype = AA   length = 90
FEATURE                 Location/Qualifiers
source                  1..90
                        mol_type = protein
                        organism = Homo sapiens
SEQUENCE: 8
GSHSLRYFST AVSRPGRGEP RYIAVEYVDD TQFLRFDSDA AIPRMEPREP WVEQEGPQYW    60
EWTTGYAKAN AQTDRVALRN LLRRYNQSEA                                    90

SEQ ID NO: 9            moltype = AA   length = 92
FEATURE                 Location/Qualifiers
source                  1..92
                        mol_type = protein
                        organism = Homo sapiens
SEQUENCE: 9
GSHTLQGMNG CDMGPDGRLL RGYHQHAYDG KDYISLNEDL RSWTAADTVA QITQRFYEAE    60
EYAEEFRTYL EGECLELLRR YLENGKETLQ RA                                 92

SEQ ID NO: 10           moltype = AA   length = 92
FEATURE                 Location/Qualifiers
source                  1..92
                        mol_type = protein
                        organism = Homo sapiens
SEQUENCE: 10
DPPKAHVAHH PISDHEATLR CWALGFYPAE ITLTWQRDGE EQTQDTELVE TRPAGDGTFQ    60
KWAAVVVPPG EEQRYTCHVQ HEGLPQPLIL RW                                 92

SEQ ID NO: 11           moltype = AA   length = 92
FEATURE                 Location/Qualifiers
source                  1..92
                        mol_type = protein
                        organism = Homo sapiens
SEQUENCE: 11
DPPKAHVAHH PISDHEATLR CWALGFYPAE ITLTWQRDGE EQTQDTELVE TRPAGDGTFQ    60
KWAAVVVPSG EEQRYTCHVQ HEGLPQPLIL RW                                 92

SEQ ID NO: 12           moltype = AA   length = 24
FEATURE                 Location/Qualifiers
source                  1..24
                        mol_type = protein
                        organism = Homo sapiens
SEQUENCE: 12
VGIVAGLVVL GAVVTGAVVA AVMW                                          24

SEQ ID NO: 13           moltype = AA   length = 17
FEATURE                 Location/Qualifiers
source                  1..17
                        mol_type = protein
                        organism = Homo sapiens
SEQUENCE: 13
RKKSSDRNRG SYSQAAV                                                  17

SEQ ID NO: 14           moltype = AA   length = 113
FEATURE                 Location/Qualifiers
source                  1..113
                        mol_type = protein
                        organism = Homo sapiens
SEQUENCE: 14
```

```
RKKSSDRNRG SYSQAAAYSV VSGNLMITWW SSLFLLGVLF QGYLGCLRSH SVLGRRKVGD    60
MWILFFLWLW TSFNTAFLAL QSLRFGFGFR RGRSFLLRSW HHLMKRVQIK IFD          113

SEQ ID NO: 15           moltype = AA  length = 93
FEATURE                 Location/Qualifiers
source                  1..93
                        mol_type = protein
                        organism = Homo sapiens
SEQUENCE: 15
IQVYSRHPAE NGKSNFLNCY VSGFHPSDIE VDLLKNGERI EKVEHSDLSF SKDWSFYLLY    60
YTEFTPTEKD EYACRVNHVT LSQPKIVKWD RDM                                93

SEQ ID NO: 16           moltype = AA  length = 15
FEATURE                 Location/Qualifiers
REGION                  1..15
                        note = Synthetic
source                  1..15
                        mol_type = protein
                        organism = synthetic construct
SEQUENCE: 16
GGIGSGGGGS GGGGS                                                    15

SEQ ID NO: 17           moltype = AA  length = 550
FEATURE                 Location/Qualifiers
REGION                  1..550
                        note = Synthetic
source                  1..550
                        mol_type = protein
                        organism = synthetic construct
SEQUENCE: 17
MAPRSLLLLL SGALALTDTW AGSHSLRYFS TAVSRPGRGE PRYIAVEYVD DTQFLRFDSD    60
AAIPRMEPRE PWVEQEGPQY WEWTTGYAKA NAQTDRVALR NLLRRYNQSE AGSHTLQGMN   120
GCDMGPDGRL LRGYHQHAYD GKDYISLNED LRSWTAADTV AQITQRFYEA EEYAEEFRTY   180
LEGECLELLR RYLENGKETL QRADPPKAHV AHHPISDHEA TLRCWALGFY PAEITLTWQR   240
DGEEQTQDTE LVETRPAGDG TFQKWAAVVV PPGEEQRYTC HVQHEGLPQP LILRWGGIGS   300
GGGGSGGGGS IQVYSRHPAE NGKSNFLNCY VSGFHPSDIE VDLLKNGERI EKVEHSDLSF   360
SKDWSFYLLY YTEFTPTEKD EYACRVNHVT LSQPKIVKWD RDMEQSPQPT IPIVGIVAGL   420
VVLGAVVTGA VVAAVMWRKK SSDRNRGSYS QAAAYSVVSG NLMITWWSSL FLLGVLFQGY   480
LGCLRSHSVL GRRKVGDMWI LFFLWLWTSF NTAFLALQSL RFGFGFRRGR SFLLRSWHHL   540
MKRVQIKIFD                                                         550

SEQ ID NO: 18           moltype = AA  length = 550
FEATURE                 Location/Qualifiers
REGION                  1..550
                        note = Synthetic
source                  1..550
                        mol_type = protein
                        organism = synthetic construct
SEQUENCE: 18
MAPRSLLLLL SGALALTDTW AGSHSLRYFS TAVSRPGRGE PRYIAVEYVD DTQFLRFDSD    60
AAIPRMEPRE PWVEQEGPQY WEWTTGYAKA NAQTDRVALR NLLRRYNQSE AGSHTLQGMN   120
GCDMGPDGRL LRGYHQHAYD GKDYISLNED LRSWTAADTV AQITQRFYEA EEYAEEFRTY   180
LEGECLELLR RYLENGKETL QRADPPKAHV AHHPISDHEA TLRCWALGFY PAEITLTWQR   240
DGEEQTQDTE LVETRPAGDG TFQKWAAVVV PSGEEQRYTC HVQHEGLPQP LILRWGGIGS   300
GGGGSGGGGS IQVYSRHPAE NGKSNFLNCY VSGFHPSDIE VDLLKNGERI EKVEHSDLSF   360
SKDWSFYLLY YTEFTPTEKD EYACRVNHVT LSQPKIVKWD RDMEQSPQPT IPIVGIVAGL   420
VVLGAVVTGA VVAAVMWRKK SSDRNRGSYS QAAAYSVVSG NLMITWWSSL FLLGVLFQGY   480
LGCLRSHSVL GRRKVGDMWI LFFLWLWTSF NTAFLALQSL RFGFGFRRGR SFLLRSWHHL   540
MKRVQIKIFD                                                         550

SEQ ID NO: 19           moltype = DNA  length = 1653
FEATURE                 Location/Qualifiers
misc_feature            1..1653
                        note = Synthetic
source                  1..1653
                        mol_type = other DNA
                        organism = synthetic construct
SEQUENCE: 19
atggcgcccc gaagcctcct cctgctgctc tcaggggccc tggccctgac cgatacttgg    60
gcgggctccc actccttgag gtatttcagc accgctgtgt cgcggcccgg ccgcggggag   120
ccccgctaca tcgccgtgga gtacgtagac acacgcaat tcctgcggtt cgacagcgac   180
gccgcgattc cgaggatgga gccgcgggag ccgtgggtgg agcaagaggg gccgcagtat   240
tgggagtgga ccacagggta cgccaaggcc aacgcacaga ctgaccgagt ggccctgagg   300
aacctgctcc gccgctacaa ccagagcgag gctgggtctc acaccctgca gggaatgaat   360
ggctgcgaca tggggcccga cggacgcctc ctccgcgggt atcaccagca cgcgtacgac   420
ggcaaggatt acatctccct gaacgaggac ctggctcctg gaccgcggc ggacaccgtg   480
gctcagatca cccagcgctt ctatgaggca gaggaatatg cagaggagtt caggacctac   540
ctggagggcg agtgcctgga gttgctccgc agatacttgg agaatgggaa ggagacgcta   600
cagcgcgcag atcctccaaa ggcacacgtt gcccaccacc ccatctctga ccatgaggcc   660
```

```
accctgaggt gctgggccct gggcttctac cctgcggaga tcacgctgac ctggcagcgg    720
gatgggagg aacagaccca ggacacagag cttgtggaga ccaggcctgc agggatgga      780
accttccaga agtgggccgc tgtggtggtg cctcctggag aggaacagag atacacatgc    840
catgtgcagc acgaggggct gccccagccc ctcatcctga gatggggggg gatcggatcc    900
ggaggcggtg gatccggtgg cggcggttcg attcaggttt actcacgtca tccagcagag    960
aatgaaaagt caaatttcct gaattgctat gtgtctgggt ttcatccatc cgacattgaa    1020
gttgacttac tgaagaatgg agagagaatt gaaaaagtgg agcattcaga cttgtctttc    1080
agcaaggact ggtctttcta tctcttgtac tacactgaat tcacccccac tgaaaaagat    1140
gagtatgcct gccgtgtgaa ccatgtgact ttgtcacagc ccaagatagt taagtgggat    1200
cgagacatgg agcagtctcc ccagcccacc atcccatcg tgggcatcgt tgctggcctt     1260
gttgtccttg gagctgtggt cactggagct gtggtcgctg ctgtgatgtg gaggaagaag    1320
agctcagata gaaacagagg gagctactct caggctgcag cctactcagt ggtcagcgga    1380
aacttgatga taacatggtg gtcaagctta tttctcctgg gggtgctctt ccaaggatat    1440
tgggctgcc tccggagtca cagtgtcttg ggccgccaga aggtgggtga catgtggatc      1500
ttgtttttttt tgtggctgtg gacatctttc aacactgcct tcttggcctt gcaaagcctt   1560
cgctttggct tcggctttag gaggggcagg agcttcctc ttcgttcttg gcaccatctt     1620
atgaaaaggg tccagattaa gattttttgac tga                                1653

SEQ ID NO: 20        moltype = AA length = 413
FEATURE              Location/Qualifiers
REGION               1..413
                     note = Synthetic
source               1..413
                     mol_type = protein
                     organism = synthetic construct
SEQUENCE: 20
MAPRSLLLLL SGALALTDTW AGSHSLRYFS TAVSRPGRGE PRYIAVEYVD DTQFLRFDSD     60
AAIPRMEPRE PWVEQEGPQY WEWTTGYAKA NAQTDRVALR NLLRRYNQSE AGSHTLQGMN   120
GCDMGPDGRL LRGYHQHAYD GKDYISLNED LRSWTAADTV AQITQRFYEA EEYAEEFRTY    180
LEGECLELLR RYLENGKETL QRADPPKAHV AHHPISDHEA TLRCWALGFY PAEITLTWQR   240
DGEEQTQDTE LVETRPAGDG TFQKWAAVVV PPGEEQRYTC HVQHEGLPQP LILRWGGIGS   300
GGGGSGGGGS IQVYSRHPAE NGKSNFLNCY VSGFHPSDIE VDLLKNGERI EKVEHSDLSF    360
SKDWSFYLLY YTEFTPTEKD EYACRVNHVT LSQPKIVKWD RDMEQSPQPT IPI          413

SEQ ID NO: 21        moltype = AA length = 413
FEATURE              Location/Qualifiers
REGION               1..413
                     note = Synthetic
source               1..413
                     mol_type = protein
                     organism = synthetic construct
SEQUENCE: 21
MAPRSLLLLL SGALALTDTW AGSHSLRYFS TAVSRPGRGE PRYIAVEYVD DTQFLRFDSD     60
AAIPRMEPRE PWVEQEGPQY WEWTTGYAKA NAQTDRVALR NLLRRYNQSE AGSHTLQGMN   120
GCDMGPDGRL LRGYHQHAYD GKDYISLNED LRSWTAADTV AQITQRFYEA EEYAEEFRTY    180
LEGECLELLR RYLENGKETL QRADPPKAHV AHHPISDHEA TLRCWALGFY PAEITLTWQR   240
DGEEQTQDTE LVETRPAGDG TFQKWAAVVV PSGEEQRYTC HVQHEGLPQP LILRWGGIGS   300
GGGGSGGGGS IQVYSRHPAE NGKSNFLNCY VSGFHPSDIE VDLLKNGERI EKVEHSDLSF    360
SKDWSFYLLY YTEFTPTEKD EYACRVNHVT LSQPKIVKWD RDMEQSPQPT IPI          413

SEQ ID NO: 22        moltype = AA length = 338
FEATURE              Location/Qualifiers
source               1..338
                     mol_type = protein
                     organism = Homo sapiens
SEQUENCE: 22
MVVMAPRTLF LLLSGALTLT ETWAGSHSMR YFSAAVSRPG RGEPRFIAMG YVDDTQFVRF     60
DSDSACPRME PRAPWVEQEG PEYWEEETRN TKAHAQTDRM NLQTLRGYYN QSEASSHTLQ   120
WMIGCDLGSD GRLLRGYEQY AYDGKDYLAL NEDLRSWTAA DTAAQISKRK CEAANVAEQR   180
RAYLEGTCVE WLHRYLENGK EMLQRADPPK THVTHHPVFD YEATLRCWAL GFYPAEIILT    240
WQRDGEDQTQ DVELVETRPA GDGTFQKWAA VVVPSGEEQR YTCHVQHEGL PEPLMLRWKQ   300
SSLPTIPIMG IVAGLVVLAA VVTGAAVAAV LWRKKSSD                           338

SEQ ID NO: 23        moltype = DNA length = 1017
FEATURE              Location/Qualifiers
source               1..1017
                     mol_type = genomic DNA
                     organism = Homo sapiens
SEQUENCE: 23
atggtggtca tggcgcccg aaccctcttc ctgctgctct cggggcct gaccctgacc        60
gagacctggg cgggctccca ctccatgagg tatttcagcg ccgccgtgtc ccggccggc    120
cgcggggagc cccgcttcat cgccatgggc tacgtggacg acacgcagtt cgtgcggttc    180
gacagcgact cggcgtgtcc gaggatggag ccgcggcgc cgtgggtgga gcaggagggg    240
ccggagtatt gggaagagga gacacggaac accaaggcgc acgcacagac tgacagaatg    300
aacctgcaga ccctgcgcgg ctactacaac cagagcgagg ccagttctca caccctccag    360
tggatgattg gctgcgacct ggggtccgac ggacgcctcc tccgcgggta tgaacagtat    420
gcctacgatg caaggattta cctcgccctg aacgaggacc tgcgctcctg gaccgcagcg    480
gacactgcgc tcagatctc caagcgcaag tgtgaggcgg ccaatgtggc tgaacaaagg    540
agagcctacc tggagggcac gtgcgtggag tggctccaca gatacctgga gaacgggaag    600
```

```
gagatgctgc agcgcgcgga ccccccaag acacacgtga cccaccaccc tgtctttgac    660
tatgaggcca ccctgaggtg ctgggccctg ggcttctacc ctgcggagat catactgacc    720
tggcagcggg atggggagga ccagacccag gacgtggagc tcgtggagac caggcctgca    780
ggggatggaa ccttccagaa gtgggcagct gtggtggtgc cttctggaga ggagcagaga    840
tacacgtgcc atgtgcagca tgaggggctg ccggagccc tcatgctgag atggaagcag    900
tcttccctgc ccaccatccc catcatgggg atcgttgctg gcctggttgt ccttgcagct    960
gtagtcactg gagctgcggt cgctgctgtg ctgtggagaa agaagagctc agattga      1017

SEQ ID NO: 24           moltype = AA  length = 90
FEATURE                 Location/Qualifiers
source                  1..90
                        mol_type = protein
                        organism = Homo sapiens
SEQUENCE: 24
GSHSMRYFSA AVSRPGRGEP RFIAMGYVDD TQFVRFDSDS ACPRMEPRAP WVEQEGPEYW    60
EEETRNTKAH AQTDRMNLQT LRGYYNQSEA                                    90

SEQ ID NO: 25           moltype = AA  length = 92
FEATURE                 Location/Qualifiers
source                  1..92
                        mol_type = protein
                        organism = Homo sapiens
SEQUENCE: 25
SSHTLQWMIG CDLGSDGRLL RGYEQYAYDG KDYLALNEDL RSWTAADTAA QISKRKCEAA    60
NVAEQRRAYL EGTCVEWLHR YLENGKEMLQ RA                                  92

SEQ ID NO: 26           moltype = AA  length = 92
FEATURE                 Location/Qualifiers
source                  1..92
                        mol_type = protein
                        organism = Homo sapiens
SEQUENCE: 26
DPPKTHVTHH PVFDYEATLR CWALGFYPAE IILTWQRDGE DQTQDVELVE TRPAGDGTFQ    60
KWAAVVVPSG EEQRYTCHVQ HEGLPEPLML RW                                  92

SEQ ID NO: 27           moltype = AA  length = 24
FEATURE                 Location/Qualifiers
source                  1..24
                        mol_type = protein
                        organism = Homo sapiens
SEQUENCE: 27
MGIVAGLVVL AAVVTGAAVA AVLW                                           24

SEQ ID NO: 28           moltype = AA  length = 6
FEATURE                 Location/Qualifiers
source                  1..6
                        mol_type = protein
                        organism = Homo sapiens
SEQUENCE: 28
RKKSSD                                                                6

SEQ ID NO: 29           moltype = AA  length = 446
FEATURE                 Location/Qualifiers
REGION                  1..446
                        note = Synthetic
source                  1..446
                        mol_type = protein
                        organism = synthetic construct
SEQUENCE: 29
MVVMAPRTLF LLLSGALTLT ETWAGSHSMR YFSAAVSRPG RGEPRFIAMG YVDDTQFVRF    60
DSDSACPRME PRAPWVEQEG PEYWEEETRN TKAHAQTDRM NLQTLRGYYN QSEASSHTLQ   120
WMIGCDLGSD GRLLRGYEQY AYDGKDYLAL NEDLRSWTAA DTAAQISKRK CEAANVAEQR   180
RAYLEGTCVE WLHRYLENGK EMLQRADPPK THVTHHPVFD YEATLRCWAL GFYPAEIILT   240
WQRDGEDQTQ DVELVETRPA GDGTFQKWAA VVVPSGEEQR YTCHVQHEGL PEPLMLRWGG   300
IGSGGGGSGG GGSIQVYSRH PAENGKSNFL NCYVSGFHPS DIEVDLLKNG ERIEKVEHSD   360
LSFSKDWSFY LLYYTEFTPT EKDEYACRVN HVTLSQPKIV KWDRDMKQSS LPTIPIMGIV   420
AGLVVLAAVV TGAAVAAVLW RKKSSD                                        446

SEQ ID NO: 30           moltype = DNA  length = 1341
FEATURE                 Location/Qualifiers
misc_feature            1..1341
                        note = Synthetic
source                  1..1341
                        mol_type = other DNA
                        organism = synthetic construct
SEQUENCE: 30
atggtggtca tggcgcccg aaccctcttc ctgctgctct cgggggccct gaccctgacc     60
gagacctggg cgggctccca ctccatgagg tatttcagcg ccgccgtgtc ccggcccggc   120
cgcggggagc ccgcttcat cgccatgggc tacgtggacg acacgcagtt cgtgcggttc   180
```

```
gacagcgact cggcgtgtcc gaggatggag ccgcgggcgc cgtgggtgga gcaggagggg    240
ccggagtatt gggaagagga gacacggaac accaaggccc acgcacagac tgacagaatg    300
aacctgcaga ccctgcgcgg ctactacaac cagagcgagg ccagttctca caccctccag    360
tggatgattg gctgcgacct ggggtccgac ggacgcctcc tccgcgggta tgaacagtat    420
gcctacgatg gcaaggatta cctcgccctg aacgaggacc tgcgctcctg gaccgcagcg    480
gacactgcgg ctcagatctc caagcgcaag tgtgaggcgg ccaatgtggc tgaacaaagg    540
agagcctacc tggagggcac gtgcgtggag tggctccaca gatacctgga gaacgggaag    600
gagatgctgc agcgcgcgga cccccccaag acacacgtga cccaccaccc tgtctttgac    660
tatgaggcca ccctgaggtg ctgggccctg ggcttctacc ctgcggagat catactgacc    720
tggcagcggg atggggagga ccagacccag gacgtggagc tcgtggagac caggcctgca    780
ggggatggaa ccttccagaa gtgggcagct gtggtggtgc cttctggaga ggagcagaga    840
tacacgtgcc atgtgcagca tgaggggctg ccggagcccc tcatgctgag atggggggg    900
atcggatccg gaggcggtgg atccggtggc ggcggttcga ttcaggttta ctcatcgtcat    960
ccagcagaga atggaaagtc aaatttcctg aattgctatg tgtctgggtt tcatccatcc   1020
gacattgaag ttgacttact gaagaatgga gagagaattg aaaaagtgga gcattcagac   1080
ttgtctttca gcaaggactg gtcttttcta tctcttgtact acactgaatt caccccccact   1140
gaaaaagatg agtatgcctg ccgtgtgaac catgtgactt tgtcacagcc aagatagtt    1200
aagtgggagc gagacatgaa gcagtcttcc ctgcccacca tccccatcat gggtatcgtt   1260
gctggcctgg ttgtccttgc agctgtagtc actgagctgc cggtcgctgc tgtgctgtgg   1320
agaaagaaga gctcagattg a                                             1341

SEQ ID NO: 31          moltype = AA    length = 281
FEATURE                Location/Qualifiers
source                 1..281
                       mol_type = protein
                       organism = Homo sapiens
SEQUENCE: 31
MQQPFNYPYP QIYWVDSSAS SPWAPPGTVL PCPTSVPRRP GQRRPPPPPP PPPLPPPPPP    60
PPLPPLPLPP LKKRGNHSTG LCLLVMFFMV LVALVGLGLG MFQLFHLQKE LAELRESTSQ   120
MHTASSLEKQ IGHPSPPEK KELRKVAHLT GKSNSRSMPL EWEDTYGIVL LSGVKYKKGG    180
LVINETGLYF VYSKVYFRGQ SCNNLPLSHK VYMRNSKYPQ DLVMMEGKMM SYCTTGQMWA   240
RSSYLGAVFN LTSADHLYVN VSELSLVNFE ESQTFFGLYK L                      281

SEQ ID NO: 32          moltype = DNA    length = 20
FEATURE                Location/Qualifiers
misc_feature           1..20
                       note = Synthetic
source                 1..20
                       mol_type = other DNA
                       organism = synthetic construct
SEQUENCE: 32
ttcgcctacg acggcaagga                                                20

SEQ ID NO: 33          moltype = DNA    length = 20
FEATURE                Location/Qualifiers
misc_feature           1..20
                       note = Synthetic
source                 1..20
                       mol_type = other DNA
                       organism = synthetic construct
SEQUENCE: 33
cccttctcca ggtatttgtg                                                20

SEQ ID NO: 34          moltype = DNA    length = 24
FEATURE                Location/Qualifiers
misc_feature           1..24
                       note = Synthetic
source                 1..24
                       mol_type = other DNA
                       organism = synthetic construct
SEQUENCE: 34
ggcagaggaa tatgcagagg agtt                                           24

SEQ ID NO: 35          moltype = DNA    length = 21
FEATURE                Location/Qualifiers
misc_feature           1..21
                       note = Synthetic
source                 1..21
                       mol_type = other DNA
                       organism = synthetic construct
SEQUENCE: 35
ctctgtgtcc tgggtctgtt c                                              21

SEQ ID NO: 36          moltype = DNA    length = 23
FEATURE                Location/Qualifiers
misc_feature           1..23
                       note = Synthetic
source                 1..23
                       mol_type = other DNA
```

```
                              organism = synthetic construct
SEQUENCE: 36
ttgggaagag gagacacgga aca                                              23

SEQ ID NO: 37            moltype = DNA   length = 21
FEATURE                  Location/Qualifiers
misc_feature             1..21
                         note = Synthetic
source                   1..21
                         mol_type = other DNA
                         organism = synthetic construct
SEQUENCE: 37
aggtcgcagc caatcatcca c                                                21

SEQ ID NO: 38            moltype = DNA   length = 19
FEATURE                  Location/Qualifiers
misc_feature             1..19
                         note = Synthetic
source                   1..19
                         mol_type = other DNA
                         organism = synthetic construct
SEQUENCE: 38
gagcgaggcc agtgagtaa                                                   19

SEQ ID NO: 39            moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 39
tctcccaggt agagggtctg                                                  20

SEQ ID NO: 40            moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 40
gcctccctga tctcctgtag                                                  20

SEQ ID NO: 41            moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 41
gacggaccct cagaatcact                                                  20

SEQ ID NO: 42            moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 42
ctccgagcaa aagtcaaatg                                                  20

SEQ ID NO: 43            moltype = DNA   length = 20
FEATURE                  Location/Qualifiers
misc_feature             1..20
                         note = Synthetic
source                   1..20
                         mol_type = other DNA
                         organism = synthetic construct
SEQUENCE: 43
cctagcccaa gaaggagatg                                                  20

SEQ ID NO: 44            moltype = DNA   length = 20
FEATURE                  Location/Qualifiers
misc_feature             1..20
                         note = Synthetic
source                   1..20
```

```
                    mol_type = other DNA
                    organism = synthetic construct
SEQUENCE: 44
taagtccagg ctggtgtcaa                                                    20
```